(12) United States Patent
Gold et al.

(10) Patent No.: US 8,080,023 B2
(45) Date of Patent: Dec. 20, 2011

(54) DEVICE AND METHOD FOR PERFORMING MULTIPLE ANASTOMOSES

(75) Inventors: Adam Gold, San Francisco, CA (US); David J. Danitz, Cupertino, CA (US); Karrie L. Sturtz, Campbell, CA (US)

(73) Assignee: Vitalitec International, Inc., Plymouth, MA (US)

( * ) Notice: Subject to any disclaimer, the term of this patent is extended or adjusted under 35 U.S.C. 154(b) by 1043 days.

(21) Appl. No.: 10/735,340

(22) Filed: Dec. 12, 2003

(65) Prior Publication Data

US 2005/0131432 A1   Jun. 16, 2005

(51) Int. Cl.
*A61B 17/08* (2006.01)
(52) U.S. Cl. .................. 606/153; 606/194; 606/213
(58) Field of Classification Search .............. 606/148, 606/150, 153, 194, 213
See application file for complete search history.

(56) References Cited

U.S. PATENT DOCUMENTS

| | | |
|---|---|---|
| 1,501,428 A | 7/1924 | Wisoff |
| 3,435,824 A | 4/1969 | Gamponia |
| 3,516,408 A | 6/1970 | Montanti |
| 4,168,708 A | 9/1979 | Lepley, Jr. et al. |
| 4,559,944 A | 12/1985 | Jaeger |
| 4,796,626 A | 1/1989 | DeVries |
| 4,817,287 A | 4/1989 | Arnold et al. |
| 5,122,122 A | 6/1992 | Allgood |
| 5,135,467 A | 8/1992 | Citron |
| 5,330,497 A | 7/1994 | Freitas et al. |
| 5,334,217 A * | 8/1994 | Das ............... 606/213 |
| 5,374,239 A | 12/1994 | Mischenko |
| 5,443,448 A | 8/1995 | DeVries |
| 5,447,515 A | 9/1995 | Robicsek |
| 5,501,692 A | 3/1996 | Riza |
| 5,599,329 A | 2/1997 | Gabbay |
| 5,613,976 A | 3/1997 | Agee et al. |
| 5,676,670 A | 10/1997 | Kim |
| 5,697,937 A | 12/1997 | Toma |
| 5,746,709 A | 5/1998 | Rom et al. |
| 5,769,870 A | 6/1998 | Salahieh et al. |
| 5,797,934 A | 8/1998 | Rygaard |
| 5,913,870 A | 6/1999 | DeFonzo et al. |

(Continued)

FOREIGN PATENT DOCUMENTS

DE    199 49 590 A1    6/2000

(Continued)

OTHER PUBLICATIONS

International Search report mailed on May 25, 2007, for PCT Application No. PCT/US04/41438 filed on Dec. 10, 2004, 8 pages.

(Continued)

*Primary Examiner* — Gary Jackson
*Assistant Examiner* — Michael Mendoza
(74) *Attorney, Agent, or Firm* — Bachman & LaPointe, P.C.

(57) ABSTRACT

Methods and devices for creating a seal in a vessel for performing multiple anastomoses. The device includes an expandable region at the shaft assembly distal end with a sealing membrane that spans the expandable region, and a corresponding clamping member moveable toward the expandable region. Once inserted into the vessel lumen the expandable region is deployed from a first low-profile position into a second expanded position, and positioned at the target site of the anastomoses. Movement of the distal end of the clamping member, which remains located outside the vessel, against the expanded region creates a seal at the target site allowing a blood-free, graft site area that is large enough to accommodate multiples anastomoses.

31 Claims, 21 Drawing Sheets

U.S. PATENT DOCUMENTS

| | | | |
|---|---|---|---|
| 5,921,996 | A | 7/1999 | Sherman |
| 5,925,054 | A | 7/1999 | Taylor et al. |
| 5,928,253 | A | 7/1999 | Sherman et al. |
| 5,944,730 | A | 8/1999 | Nobles et al. |
| 5,947,919 | A | 9/1999 | Krueger et al. |
| 5,954,735 | A | 9/1999 | Rygaard |
| 5,957,363 | A | 9/1999 | Heck |
| 6,015,416 | A | 1/2000 | Stefanchik et al. |
| 6,017,352 | A | 1/2000 | Nash et al. |
| 6,030,406 | A | 2/2000 | Davis et al. |
| 6,042,563 | A | 3/2000 | Morejohn et al. |
| 6,071,297 | A | 6/2000 | Salahieh et al. |
| 6,095,997 | A | 8/2000 | French et al. |
| 6,113,613 | A | 9/2000 | Spaulding |
| 6,132,440 | A | 10/2000 | Hathaway et al. |
| 6,135,981 | A | 10/2000 | Dyke |
| 6,143,015 | A | 11/2000 | Nobles |
| 6,149,583 | A | 11/2000 | Vierra et al. |
| 6,171,319 | B1 | 1/2001 | Nobles et al. |
| 6,183,486 | B1 | 2/2001 | Snow et al. |
| 6,187,019 | B1 | 2/2001 | Stefanchik et al. |
| 6,190,357 | B1 | 2/2001 | Ferrari et al. |
| 6,203,559 | B1 | 3/2001 | Davis et al. |
| 6,210,365 | B1 | 4/2001 | Afzal |
| 6,214,022 | B1 | 4/2001 | Taylor et al. |
| 6,579,311 | B1 | 6/2003 | Makower |
| 6,620,177 | B2 | 9/2003 | Buelna et al. |
| 6,652,556 | B1 * | 11/2003 | VanTassel et al. ............ 606/200 |
| 6,786,898 | B2 | 9/2004 | Guenst |
| 2002/0173801 | A1 | 11/2002 | Schulze |
| 2004/0073238 | A1 | 4/2004 | Makower |

FOREIGN PATENT DOCUMENTS

| | | |
|---|---|---|
| EP | 0 856 287 A1 | 8/1998 |
| EP | 0 894 475 A1 | 2/1999 |
| JP | 2002-500531 | 1/2002 |
| JP | 2005-529707 | 10/2005 |
| WO | WO-98/52475 A1 | 11/1998 |
| WO | WO 99/08603 A1 | 2/1999 |
| WO | WO 01/17582 A2 | 3/2001 |
| WO | WO 02/067787 A2 | 9/2002 |
| WO | WO-03/086246 A1 | 10/2003 |
| WO | WO-2004/000135 A2 | 12/2003 |
| WO | WO-2004/000135 A3 | 4/2004 |
| WO | WO-2005/059411 A2 | 6/2005 |
| WO | WO-2005/059411 A3 | 6/2005 |

OTHER PUBLICATIONS

Supplementary European Search Report mailed on Jun. 7, 2010, for EP Patent Application No. 04813707.9, filed on Dec. 10, 2004, 2 pages.

* cited by examiner

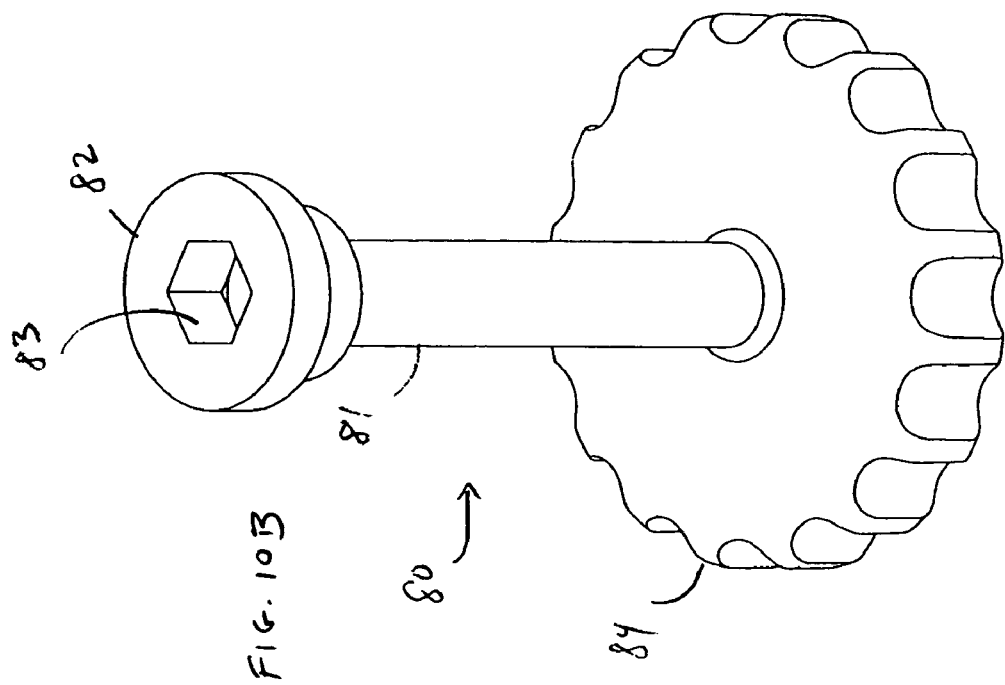
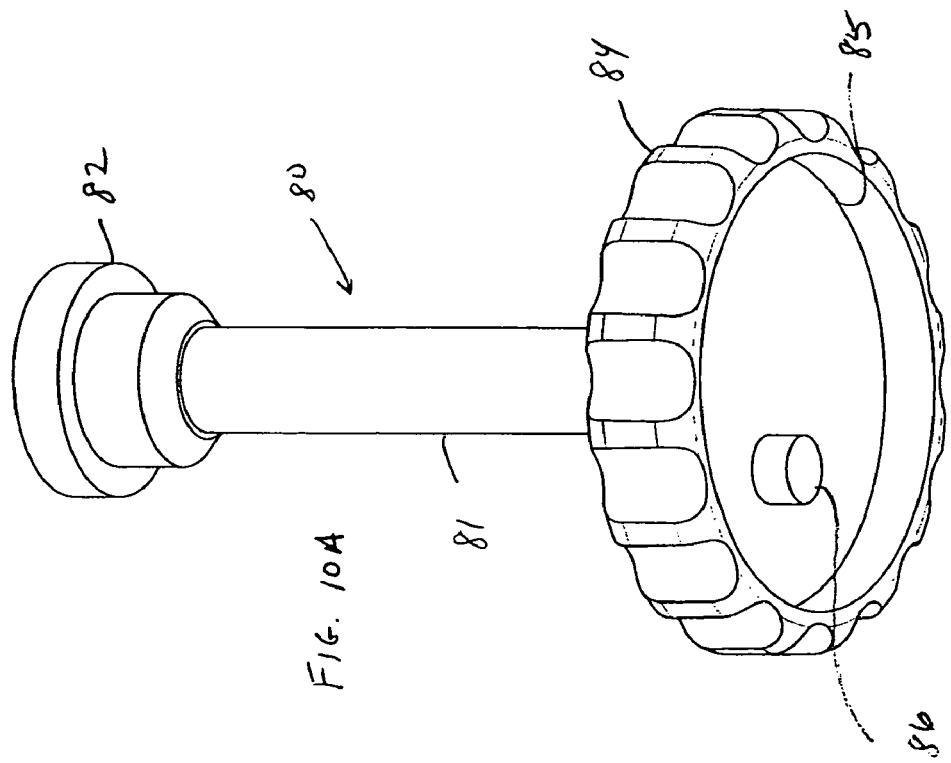

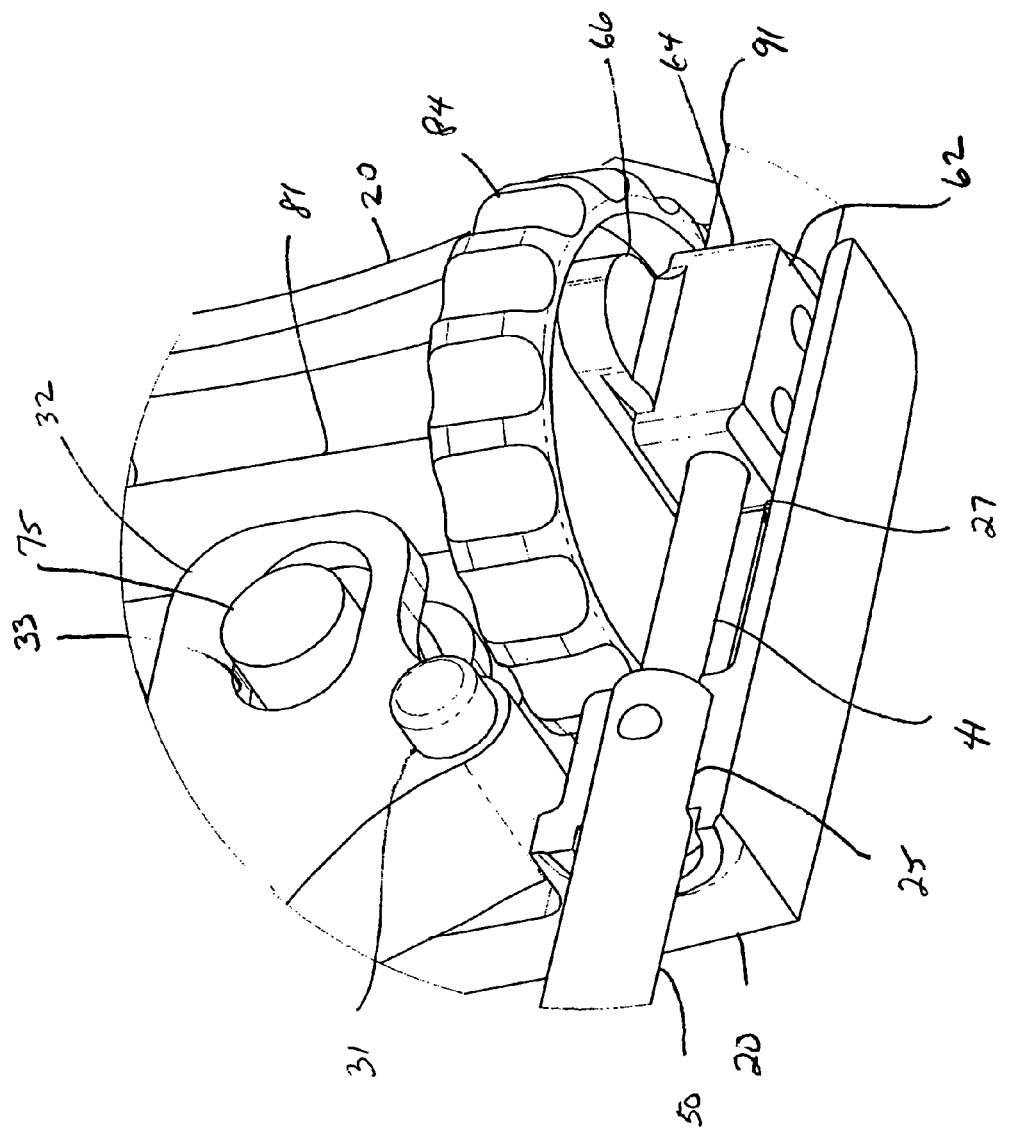

SECTION A-A

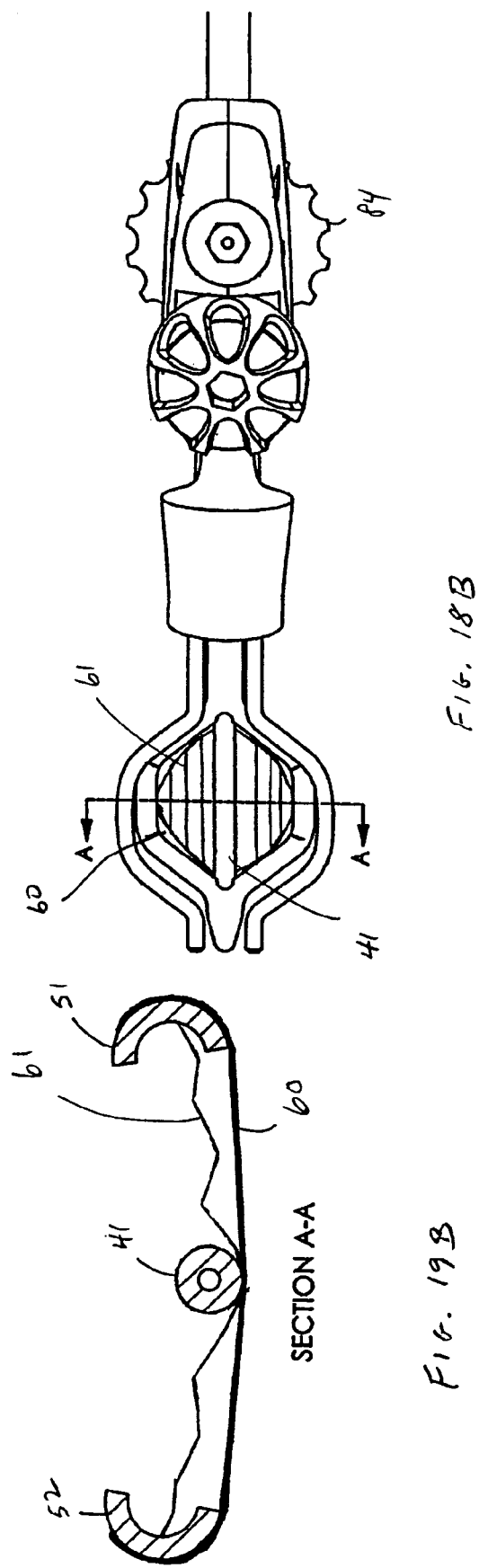

DEVICE AND METHOD FOR PERFORMING MULTIPLE ANASTOMOSES

BACKGROUND OF THE INVENTION

The present invention relates to the fields of vascular and cardiovascular surgery, and more particularly to methods and devices for obtaining hemostatic sealing when performing graft procedures.

Vascular and cardiovascular grafting procedures typically require the complete, or at least partial, occlusion of a selected vessel. For example, in the field of cardiovascular surgery, coronary artery bypass graft (CABG) procedures involving proximal anastomosis require the full, or at least partial, occlusion of the aorta. During proximal anastomosis, a vein or arterial graft is sewn to the aorta for revascularization of diseased or otherwise compromised coronary arteries. The internal mammary artery and radial artery of the arm are also used as bypass vessels. Occlusion of the aorta is typically accomplished by clamping. A variety of clamp configurations are in common use, including crossclamps for partial occlusion procedures. For procedures involving cardiopulmonary bypass, full aortic occlusion is required. Partial occlusion is used in either on or off-pump coronary artery bypass graft procedures for proximal anastomosis. Occlusion of the aorta prevents blood flow from entering the graft target site, creating a bloodless field for the surgeon to then sew the graft to the aorta. Once the graft is sewn to the aorta, the surgeon removes the clamp, once again allowing blood flow to the anastomotic region.

Unfortunately, injury resulting from such clamping can be significant. Such injuries include, but are not limited to, intimal hyperplasia, thrombosis (which may progress to total occlusion), embolism, intimal tears and flaps, mural dissections, aneurysms, arterial rupture, through-and through injury, and arterio-venous fistulae. As just one example, neurologic morbidity after cardiac surgery has been associated with particulate embolization. Crossclamp manipulation has been identified as the single most significant cause of particulate emboli release during cardiac surgery. Therefore, surgeons would prefer to eliminate the use of clamps during coronary artery bypass graft procedures in order to minimize adverse events and improve outcomes.

Efforts have been made to devise alternative devices and methods for performing bypass graft procedures that avoid complete clamping or crossclamping of the aorta. For example, U.S. Pat. No. 5,477,515 describes a bypass clamp with a spoon-shaped blade insertable through an incision in the aorta. Patches of saphaneous vein or other substitute are sutured on either side of the incision to reinforce the aorta and prevent tearing or abrasion by the clamp. U.S. Pat. No. 5,944,730 describes a device for creating a seal at an incision that includes a tube with a translatable shaft connected to a flexible inverting member. The inverting member is inserted into the incision and proximal force applied to the device creates a seal. Other methods have relied upon inflatable devices for partially occluding a vessel without interrupting blood flow. U.S. Pat. No. 6,143,015 describes such a device which includes first and second inflatable spaced apart members interconnected by a tubular connector that allows for blood flow.

WO 02/067787 describes a device having a low-profile shaft assembly that can be inserted into the lumen of a vessel with an expandable region that can be deployed into an expanded position. Movement of a corresponding clamping member which remains located outside the vessel against the expanded region creates a seal at the target site for performing an anastomosis procedure.

There remains a need for improved devices and methods for performing anastomosis procedures, including devices and methods that facilitate performing multiple. anastomoses in a simple, reliable and convenient fashion.

SUMMARY OF THE INVENTION

The present invention meets the above needs and achieves further advantages by providing for improved devices and methods for performing anastomosis procedures, including multiple anastomoses.

In an aspect of the invention, methods and devices are provided for creating a seal at a target anastomosis site in a blood vessel. The methods and devices include the use of a low profile shaft assembly configured for insertion into a blood vessel, the shaft assembly further having an expandable region and a sealing membrane spanning the expandable region, with the expandable region being deployable from a first low-profile position to a second expanded position. Methods of using the assembly include inserting the assembly into the desired blood vessel and positioning the expandable region at the target anastomosis site, then deploying the expandable region from said first low-profile position to said second expanded position and engaging the inner wall of the blood vessel at the target anastomosis site with the expandable region in its second expanded position to create a seal at the target anastomosis site. In variations of methods according to the invention, an anastomosis procedure is then performed at the sealed anastomosis site. Multiple anasotomoses can be performed by repositioning the expandable region at subsequent target sites, without withdrawing the shaft assembly from the vessel.

In another aspect of the invention, methods and devices are provided for performing multiple anastomoses that include the use of a sealing member deployable from a first low-profile position to a second expanded position. The sealing member is similarly introduced into a blood vessel, deployed its first low-profile position to said second expanded position, and engaged with the inner wall of the blood vessel at a desired location to create a seal. The sealing member is further configured such that sealed area of the blood vessel is large enough to accommodate multiple ansastomoses.

In other aspects of the invention, the deployment of shaft assemblies or sealing members according to the invention can be remotely actuated.

In a further aspect of the invention, a device for creating a seal in a blood vessel is provided having a low profile shaft assembly configured for insertion into a vessel, the shaft assembly having an expandable region at the distal end of the shaft assembly and a sealing membrane spanning the expandable region, with the expandable region being deployable from a first low-profile position to a second expanded position. The device also includes a clamping member positioned generally opposite to and moveable towards said expanding region, said clamping member having a distal end shape corresponding to said expanding region in its second expanded position. That is, the distal end corresponds in shape to the expanded region to a sufficient degree such that when expanded region is deployed within a blood vessel and the expanded region and clamping member region are compressed together, the inner wall of the blood vessel contained by the expanded region is sealed-off from continuing blood flow within the vessel. In further variations of the invention, the expanded region can correspond to a surface area of the blood vessel that is large enough to accommodate multiple anastomosis sites, allowing for performance of multiple anastomoses with a single deployment of the device. In other variations of the invention, the expanded region of the device can include a variety of shapes, including hexagonal, octagonal, oval, circular and the like.

In other variations, the expandable region of devices according to the invention further include segments that bow outwardly from the shaft assembly when the expandable region is deployed from said first low-profile position to said second expanded position. These bowing segments can further be biased toward the clamping member, to aid in efficacy of sealing. The bowing segments can be formed, e.g., of a slitted flexible tube or a super-elastic shape memory alloy.

In further variations of invention, the shaft assembly of devices according to the invention can be operably linked to a slide such that translational movement of the slide deploys the expandable region of the shaft assembly from its first low-profile position to its second expanded position. In other variations, a deployment tube moveable in relationship to the expandable region is provided such that translational movement of expandable region from deployment tube deploys the expandable region from its first low-profile position to its second expanded position.

In other variations of the invention, the integrity of the sealing membrane is protected or enhanced as a precaution against inadvertent tearing or puncture of the deployed sealing membrane during an anastomosis procedure. For example, the sealing membrane itself can be reinforced, or a protective shield can be provided that is deployable over the sealing membrane.

In yet another variation of the invention, the expandable region in its second expanded position can have a cup-shaped configuration, such that when in use it creates a sealed-off region around the rim of the cup-shaped configuration, with increased depth that allows for a larger workspace for performing the anastomosis procedure.

BRIEF DESCRIPTION OF THE DRAWINGS

FIGS. 10A and 10B are perspective views of the slide actuator of the device of FIG. 1 that engages the slide shown in FIG. 9;

FIG. 11 is a perspective view of the device of FIG. 1, with parts broken away, showing the slide, slide actuator and shaft assembly;

FIGS. 18A and 19A are top and sectional views, respectively, of a shaft assembly of a device according to a yet another embodiment of the invention in its non-deployed position, with FIG. 19A taken along plane A-A of FIG. 18A;

FIGS. 18B and 19B are top and sectional views, respectively, of the shaft assembly of the device of FIGS. 18A and 19A, in its deployed, expanded position, with FIG. 19B taken along plane A-A of FIG. 18B;

DETAILED DESCRIPTION OF THE INVENTION

Figure 1:
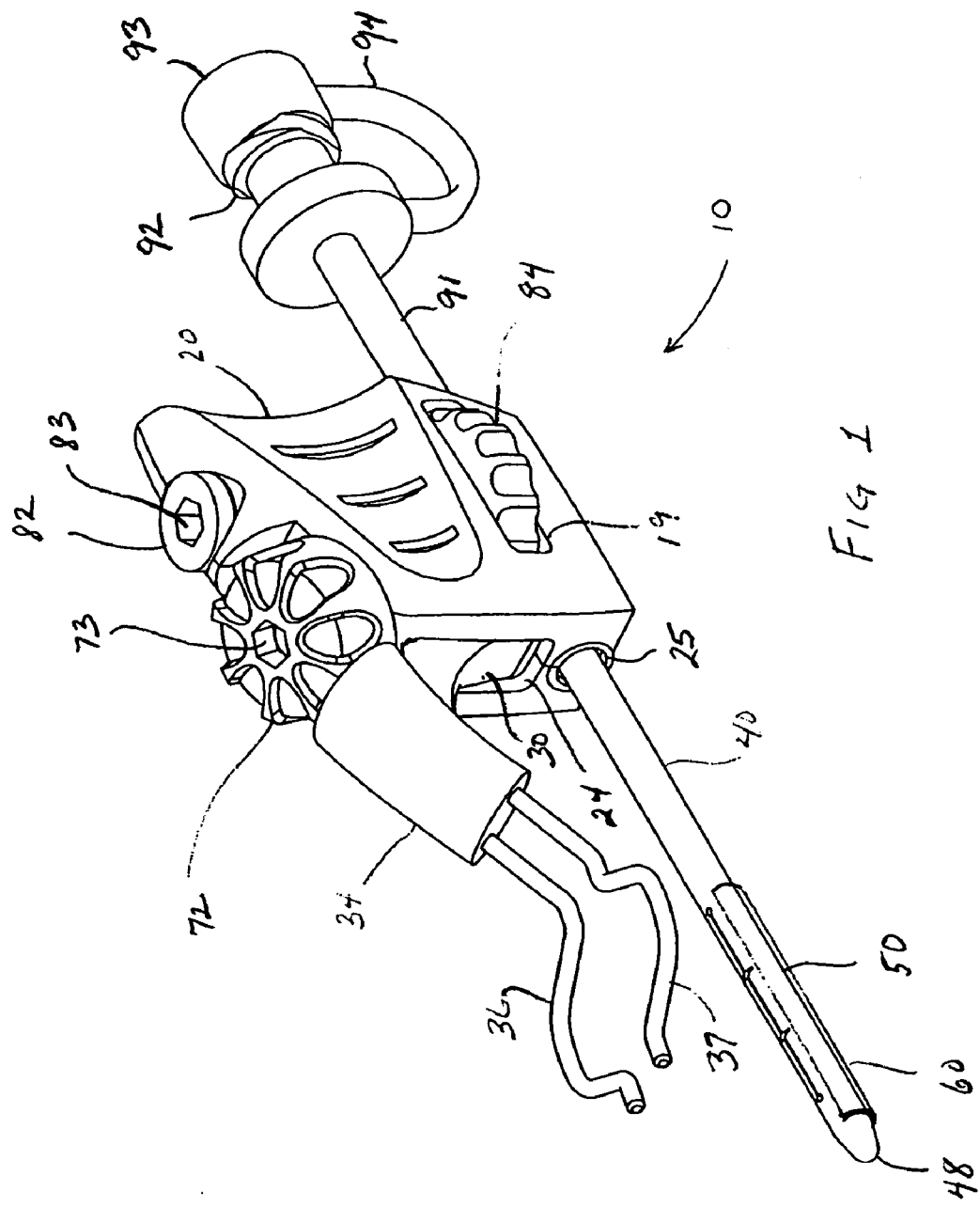
FIG. 1 is a perspective view of a device according to one embodiment of the invention, with the device in an open, non-sealing position and the expandable region of the shaft assembly of the device in an unexpanded position.

FIGS. 1-11 depict one embodiment of a device according to the present invention. Device 10 includes shaft assembly 40 and clamping member 30 extending from housing 20. As more clearly seen in FIGS. 6-7, Shaft assembly 40 includes control rod 41 disposed within flexible tube 50, with slide 62 being secured to the proximal end 47 of the rod that resides within housing 20. Slide 62 is disposed within housing 20 and is moveable along track 27 from a first to a second position relative to the housing. As seen more clearly in FIGS. 4-5, clamping member 30 is pivotally mounted to the housing at pivot 31. Clamping member 30 includes arm 34 that extends from housing 20 and terminates at its distal end in forks 36 and 37. Slide actuator 80 and clamping member actuator 70 are operably linked to slide 62 and clamping member 30, respectively, as is further described.

Figure 6:
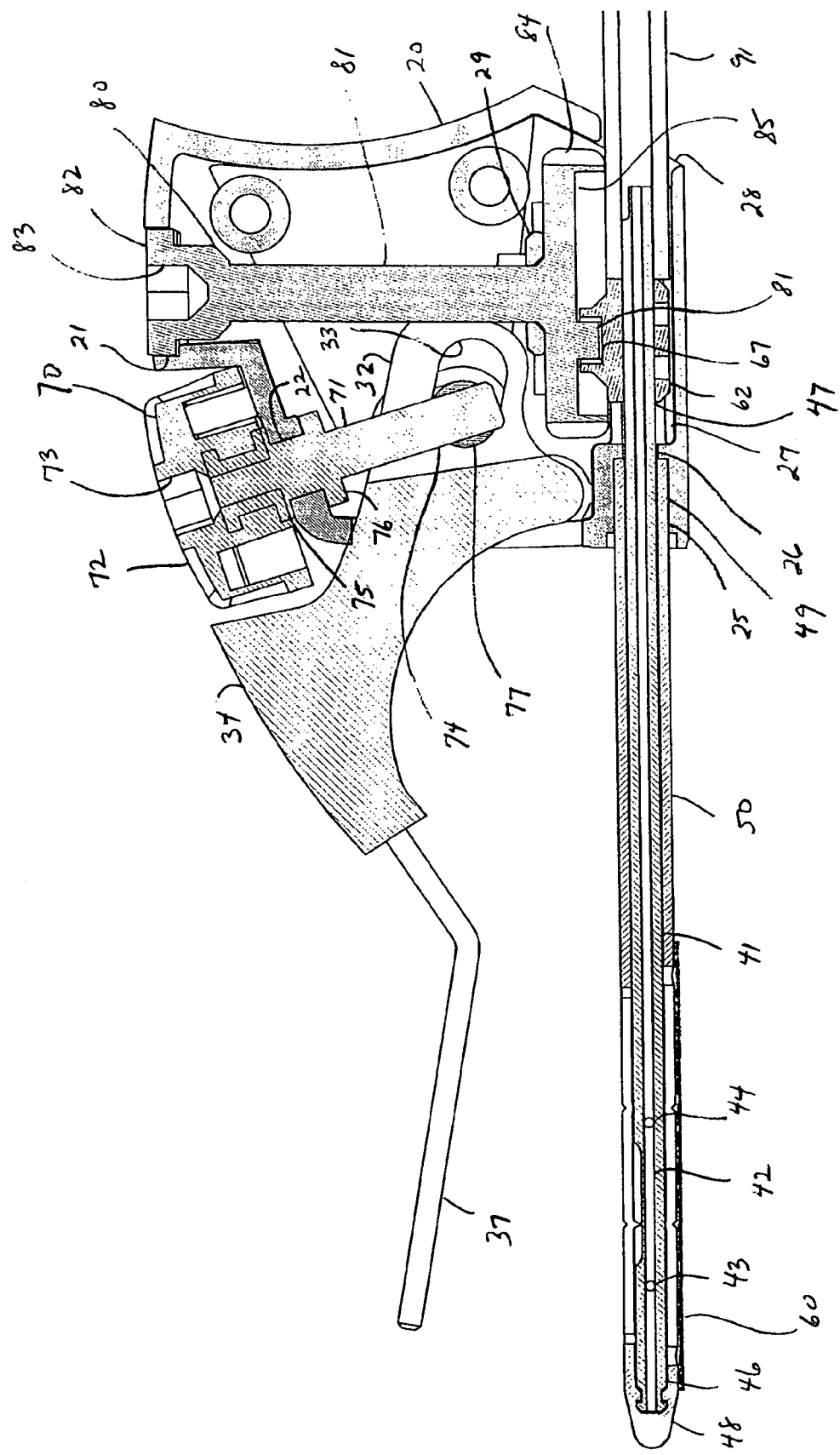
FIG. 6 is a sectional view of the device of FIG. 1 in the open, non-sealing position as shown in FIG. 1.
Figure 7:
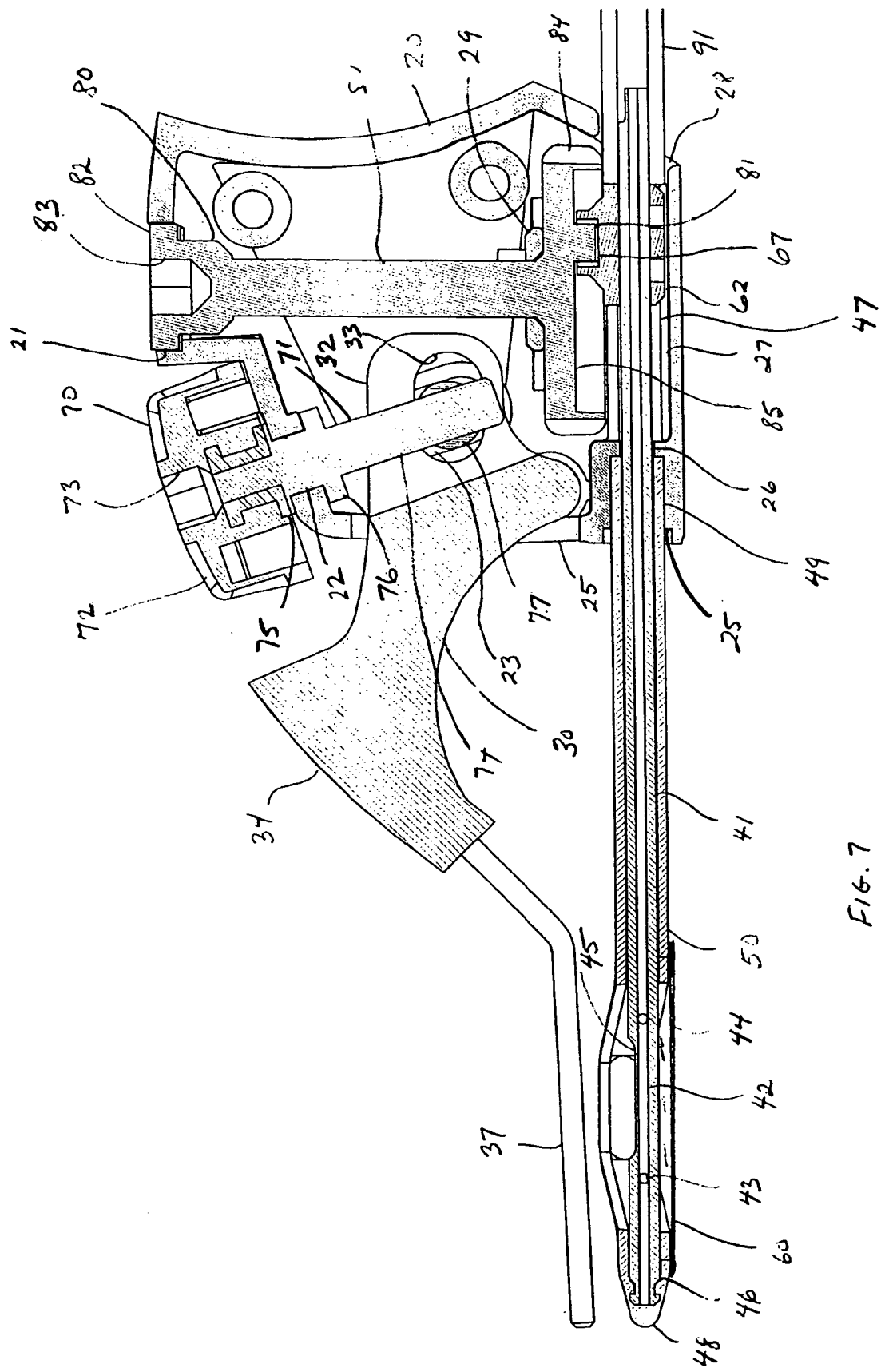
FIG. 7 is a sectional view of the device of FIG. 1 in the sealing position as shown in FIG. 3.
Figure 8:
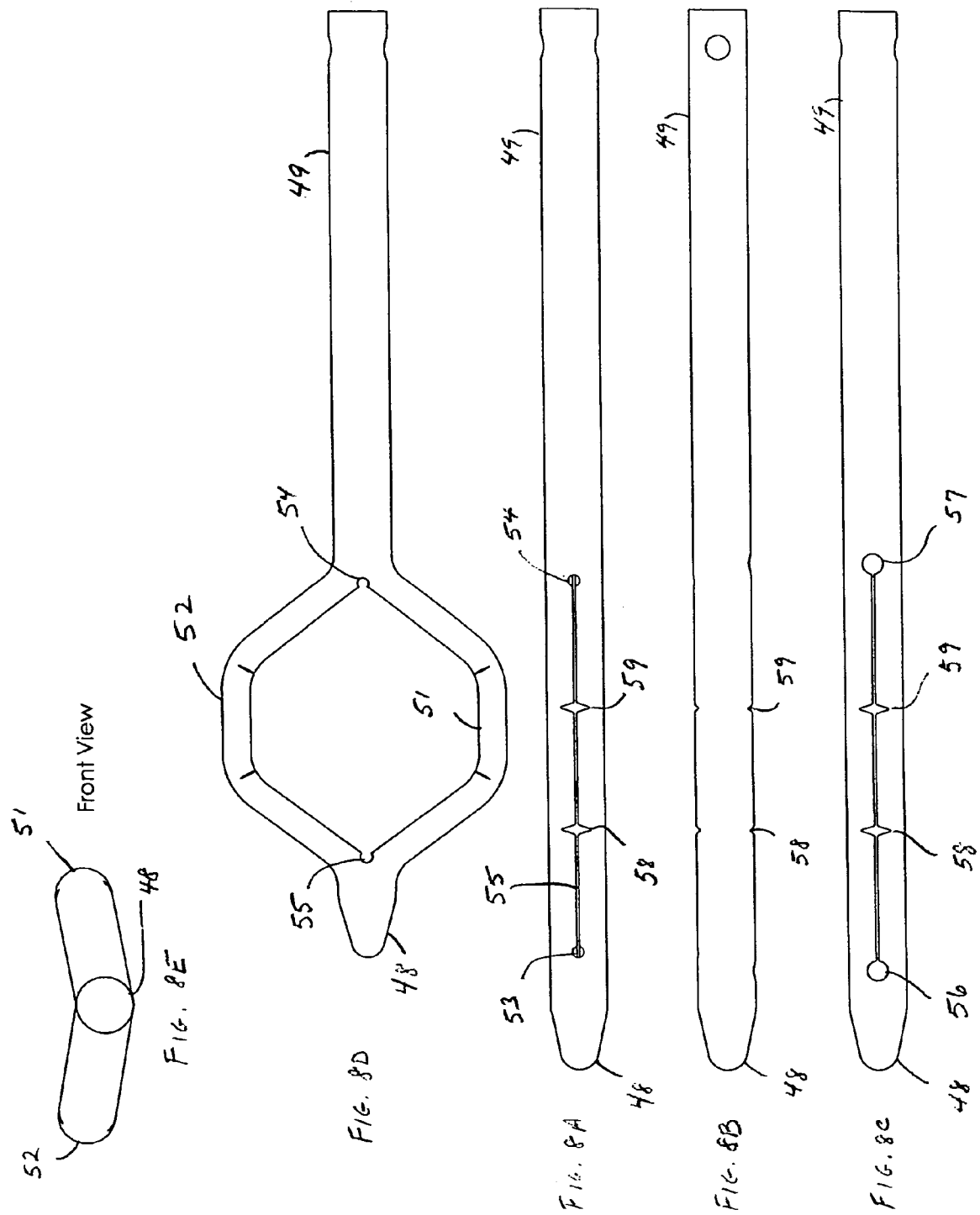
FIGS. 8A-8C are top (FIG. 8A), side (FIG. 8B) and bottom (FIG. 8C) views of the shaft assembly of the device of FIG. 1 in its unexpanded position.
FIG. 8D is a top view of the shaft assembly of the device of FIG. 1 in its deployed, expanded position.
FIG. 8E is a front view of the shaft assembly of the device of FIG. 1 in its deployed, expanded position.

As shown in FIGS. 6-7, control rod 41 of shaft assembly 40 is surrounded by flexible tube 50. Control rod 41 is preferably formed of rigid biocompatible material, such as stainless steel. Flexible tube 50 is preferably made of a plastic, such as Hytrel™, having a durometer in the range of 60-90 Shore D and a length between 1" and 3". As further depicted in FIGS.

8A-8D, Holes 53 and 54 extend through the top of tube 50 at its distal end, with hole 54 being proximal to hole 53, while holes 56 and 57 extend through the bottom of tube 50, with hole 56 being slightly distal to hole 53 and hole 57 slightly proximal to hole 54. Slot 55 extends through the tube, spanning from distal holes 53 and 56 to proximal holes 54 and 57. Notches 58 and 59, which also extend through tube, are located along slot 55 roughly one-third and two-thirds of the way between holes 53, 56 and holes 54, 57. Distal tip 46 of control rod 41, which remains located inside the flexible tube, is permanently fixed to the distal tip of flexible tube 50, but the remainder of the flexible tube is free to move axially relative to shaft assembly 40. Proximal end 49 of flexible tube 50 is received within housing 20 through opening 25 and terminates at stop 26, as shown. Flexible tube 50 is rigidly secured to housing 20 by bosses in the housing (not shown) that fit corresponding holes provided on the flexible tube (not shown). Alternatively, flexible tube 50 can otherwise be secured to housing 20, or can abut up against the housing. Sealing membrane 60 extends along at least that part of the flexible tube that includes through slot 55. Alternatively, the sealing membrane can be formed of a split tube that surrounds that part of the flexible tube, with the split portion of the tube coinciding with slot 55. The sealing membrane can be formed of a variety of elastomers, including silicone. In the depicted embodiment, the thickness of the membrane can be between 0.008" to 0.015", with the overall diameter of the shaft assembly is in the range of 0.070" to 0.110", and the overall dimensions of the device being 3.5×3.5×0.4" or less. One skilled in the art will appreciate that the dimensions can be varied to optimize performance based on the dimensions of the particular vessel to be occluded.

Figure 2:
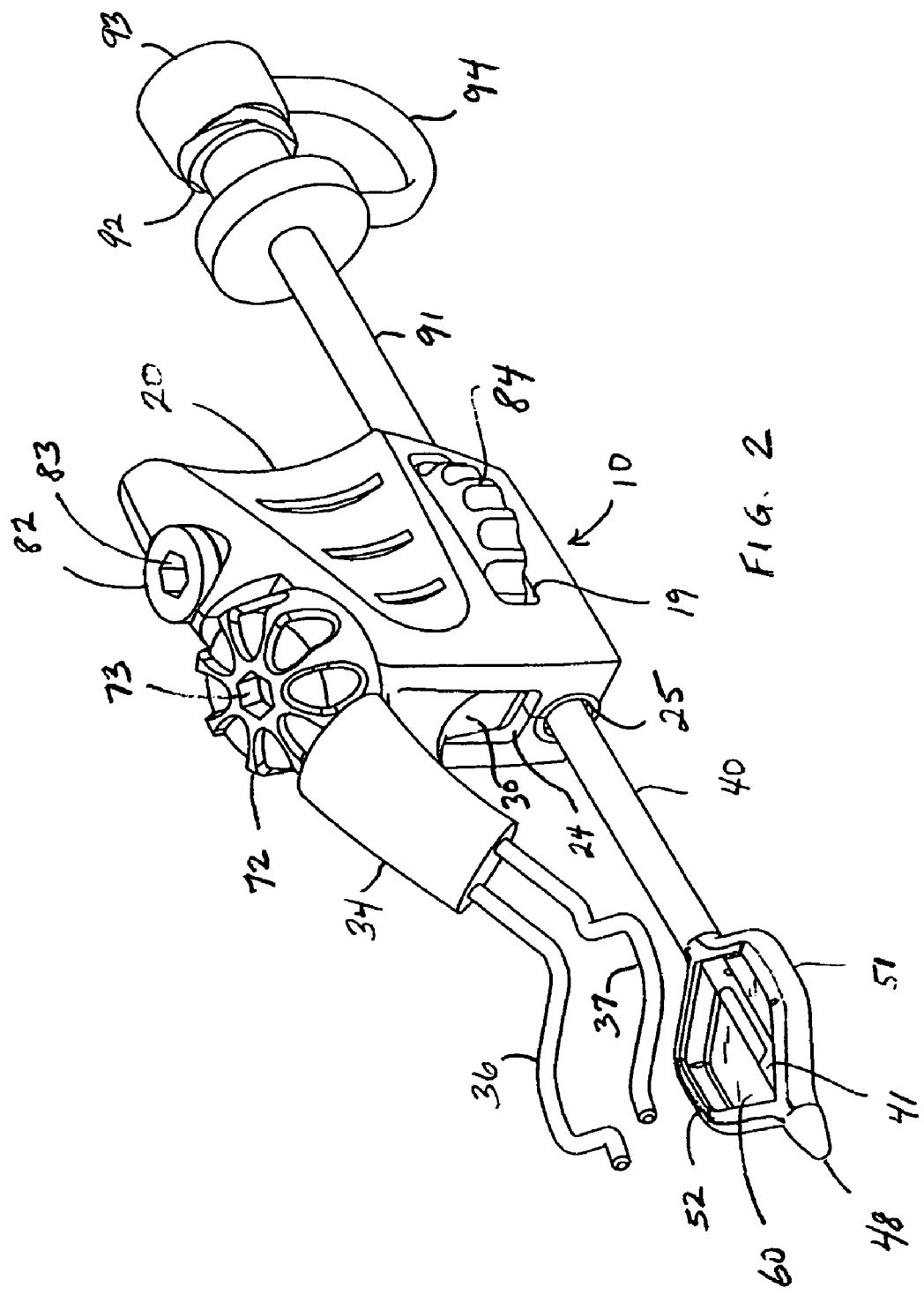
FIG. 2 is a perspective view of the device of FIG. 1, with the expandable region shaft assembly of the device in its deployed, expanded position.
Figure 3:
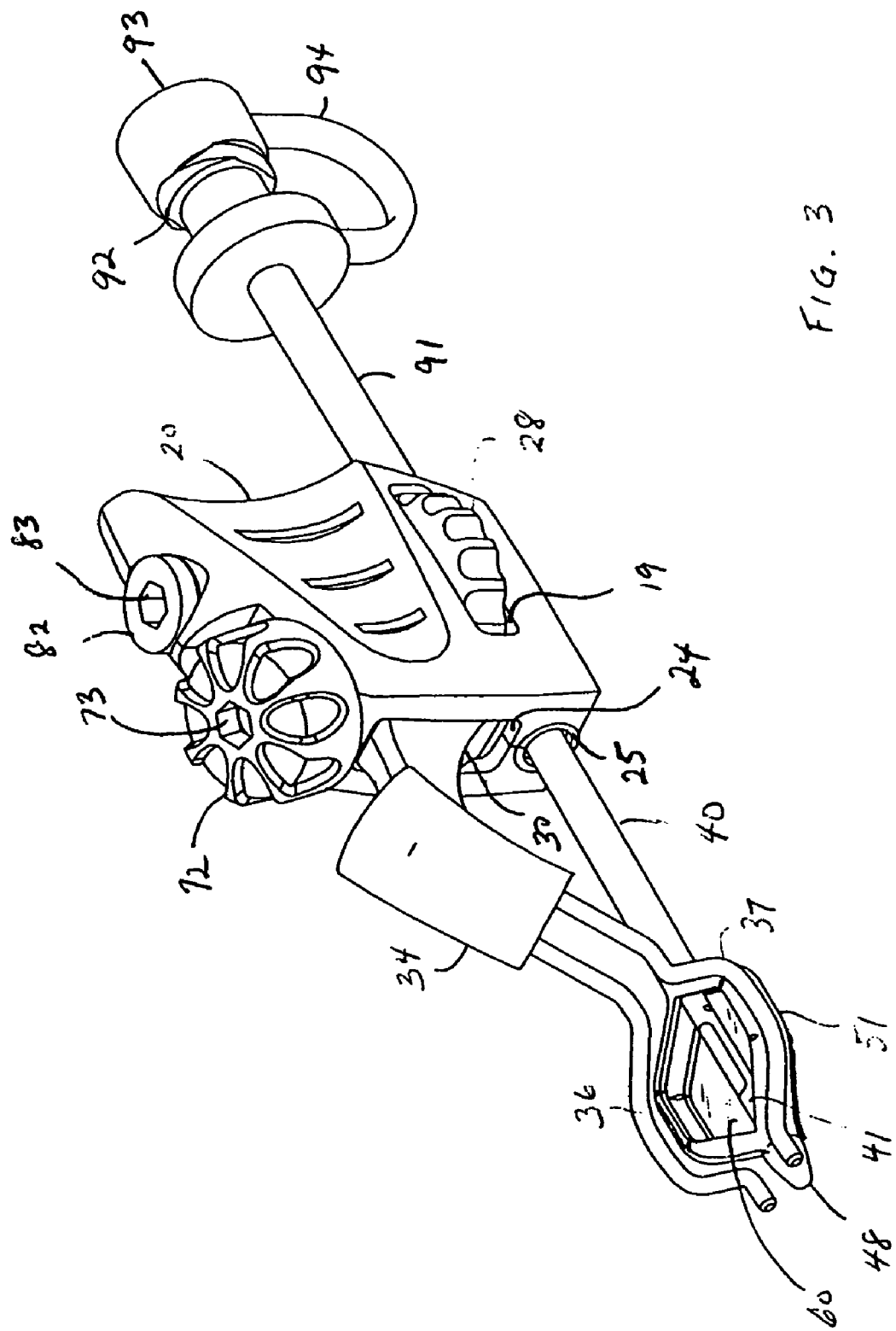
FIG. 3 is a perspective view of the device of FIG. 1 in a sealing position, with the expandable region shaft assembly of the device in its deployed, expanded position and the clamping member moved toward the shaft assembly.
Figure 4:
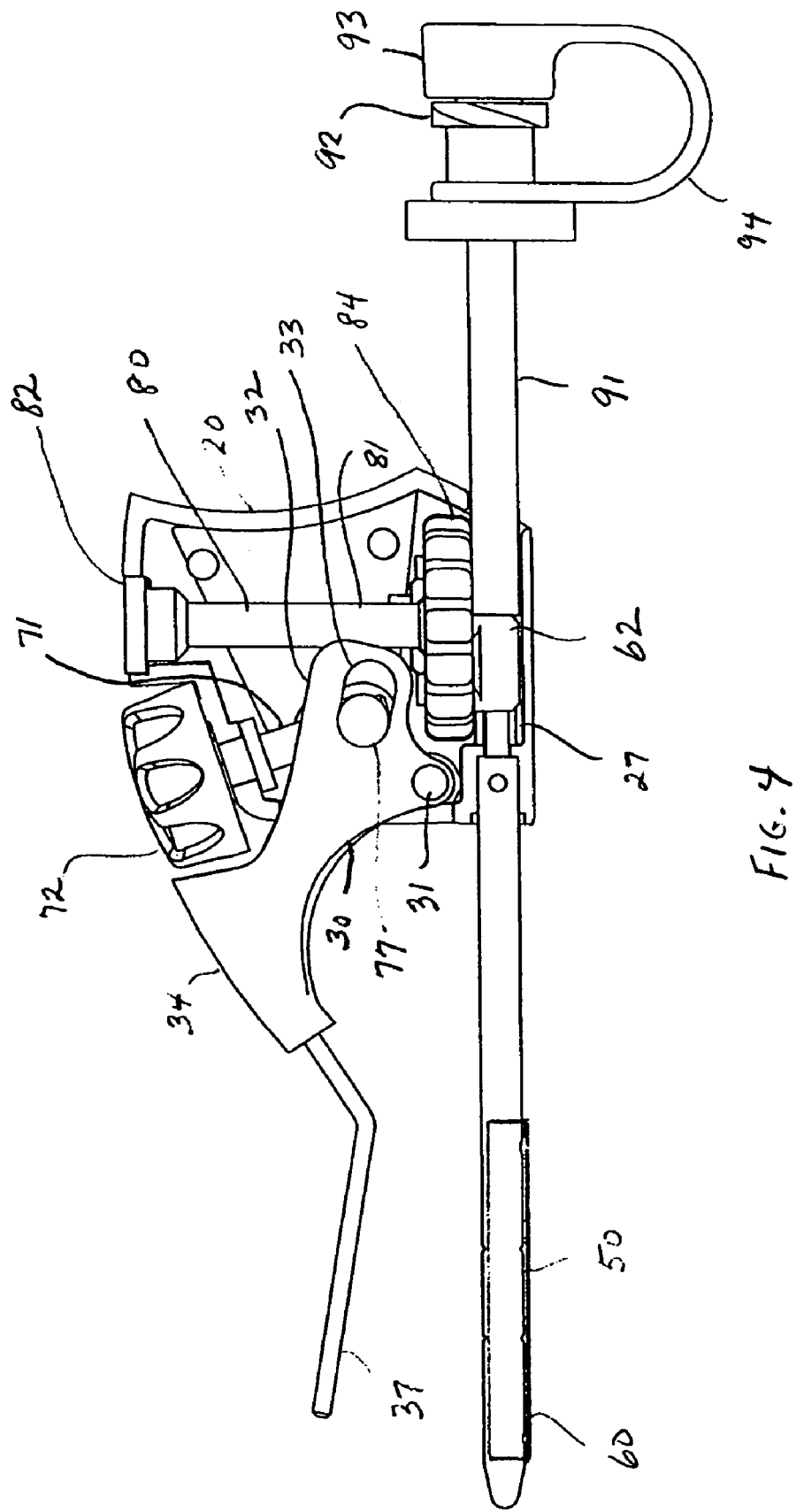
FIG. 4 is a side view of the device of FIG. 1, with parts broken away, in the open, non-sealing position as shown in FIG. 1.
Figure 5:
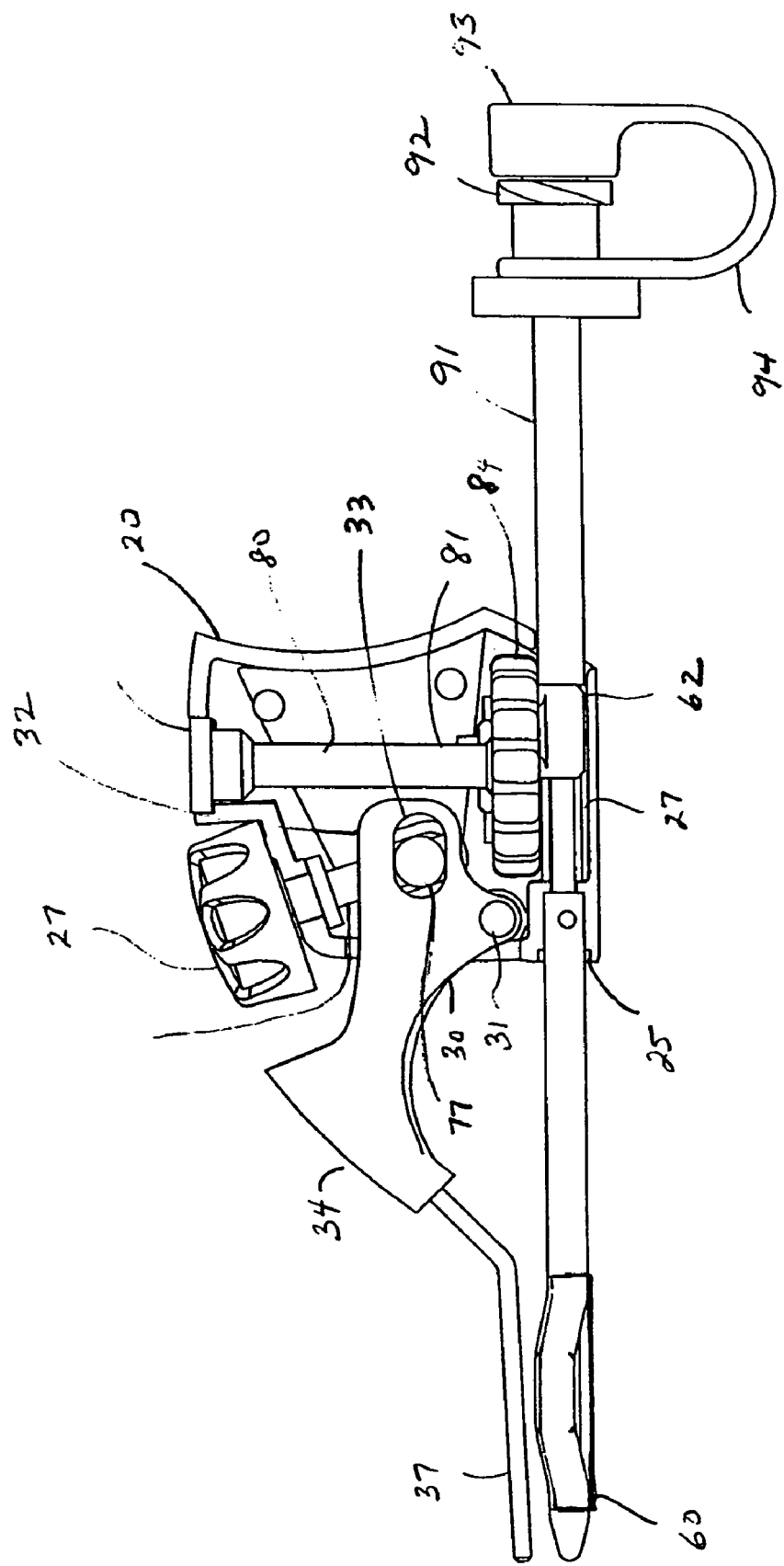
FIG. 5 is a side view of the device of FIG. 1, with parts broken away, in the sealing position as shown in FIG. 3.

FIGS. 1, 4 and 6 depict device 10 in an open, non-sealing position, with shaft assembly 40 in a low-profile, non-expanded position, while FIG. 2 depicts the shaft assembly deployed to its expanded position. FIGS. 3, 5 and 7 depict the device in its closed, sealing position, with the shaft assembly deployed in its expanded position and clamping member arm 34 and forks 36 and 37 moved toward the shaft assembly. As shown more clearly in FIGS. 4-7, lateral movement of slide 62 causes deployment of the shaft assembly from its low-profile, non-expanded position to its deployed, expanded position. Specifically, lateral translational movement of slide 62 away from the distal end of the shaft assembly results in lateral displacement of control rod 41. Displacement of control rod 41 forces distal tip 48 of flexible tube 50 to likewise displace. Proximal end 49 of flexible tube 50, however, is restrained in housing 20, so that continued displacement of the control rod causes portions 56 and 57 of the flexible tube to bow outwardly to accommodate the displacement of the distal tip, as seen in FIGS. 2, 3, 5 and 7. The provision of holes 53, 56 and 54, 57, and notches 58 and 59 weakens the relative rigidity of those corresponding regions of the tube, providing natural flex points along the two sides of the split portion of the tube, which allow for bowing portions 51 and 52 to bow outwardly from the control rod. Notches 58 and 59 are further configured to ensure formation of a hexagonal pattern. The sides of each are cut to form an angle of approximately 39 degrees. As the bowing portions move outwardly, the sides of the notches come into contact with one another, maintaining the bowing portions at prescribed angles to form a hexagon. (See FIGS. 8A-8D). Further, as has been noted, distal holes 53 and 56 are offset from one another as are proximal holes 54 and 57, with hole 54 being slightly distal to hole 53 and whole 57 being slightly proximal to hole 56. This offset contributes to a slight upward biasing of the bowing portions in the direction of the opposing forks of the clamping member, as further depicted e.g. in FIGS. 5, 7 and 8E. As will be detailed further, this biasing of the bowing portions toward the clamping member forks provides for improved sealing of the device in operation. As also seen in e.g. FIGS. 2, 3, 5 and 7, as the bowing portions expand outwardly, elastomeric sealing membrane 60 stretches to form a relatively planar sheet spanning the now expanded hexagonal region of the distal end of the shaft assembly. As more clearly shown in e.g. FIG. 3, membrane 60 is adhered to the flexible tube 50 and stretches across the underside of the expanded region, opposite clamping member forks 36, 37. As will be detailed further, in operation, this creates a working space between the sealed-off inner wall of a vessel and the membrane itself that is advantageous.

As noted, clamping member 30 is pivotally mounted to housing 20. As shown more clearly in FIGS. 4-5, the clamping member pivots around pivot pin 31 which is received in a corresponding groove (not shown) within the housing. As shown e.g. in FIGS. 2-3, arm 34 of clamping member 30 extends from the housing through opening 24. Forks 36 and 37 extend from arm 34 to form a shape that generally corresponds to that of the expanded hexagonal region of the distal end of the shaft assembly. The forks 36 and 37 of clamping member 30 are further positioned relative to the distal end of the shaft assembly such that when the arm is pivoted toward the shaft, the forks can come into contact the expanded hexagonal region. While forks 36 and 37 are depicted as likewise forming a hexagonal region, other corresponding shapes, e.g., circular shapes, will also suffice as long as such shapes correspond the expanded region shape to a sufficient degree such that when expanded region is deployed within a blood vessel and the expanded region and clamping member region are compressed together, the inner wall of the blood vessel contained by the expanded region is sealed-off from continuing blood flow within the vessel.

In operation, when the shaft assembly 40 is deployed into a vessel and forks 36 and 37 of clamping member 30 are compressed against the expanded region from the outside of the vessel, a seal is created at the clamp site. Further, by having the seal created by the membrane being stretched only across the underside of the expanded region, a small space is created between the clamped vessel wall and the stretched membrane. The provision of this space is advantageous to the surgeon, facilitating grafting procedures with less risk of puncturing the sleeve and breaking the seal. The slight upward bias of bowing portions 51 and 52 toward clamp forks 36 and 37 aids in the formation of a tight seal. In sealing operation, the bowing portions engage against the interior vessel wall opposite the clamping forks on exterior of the vessel. The compressive force applied to keep the bowing portions in place and create the seal can cause the bowing portions to deflect slightly, but by having bowing portions initially biased toward the clamping forks, a certain amount of deflection can be accommodated while still maintaining a good seal and avoiding any undesirable leakage.

Figure 9:
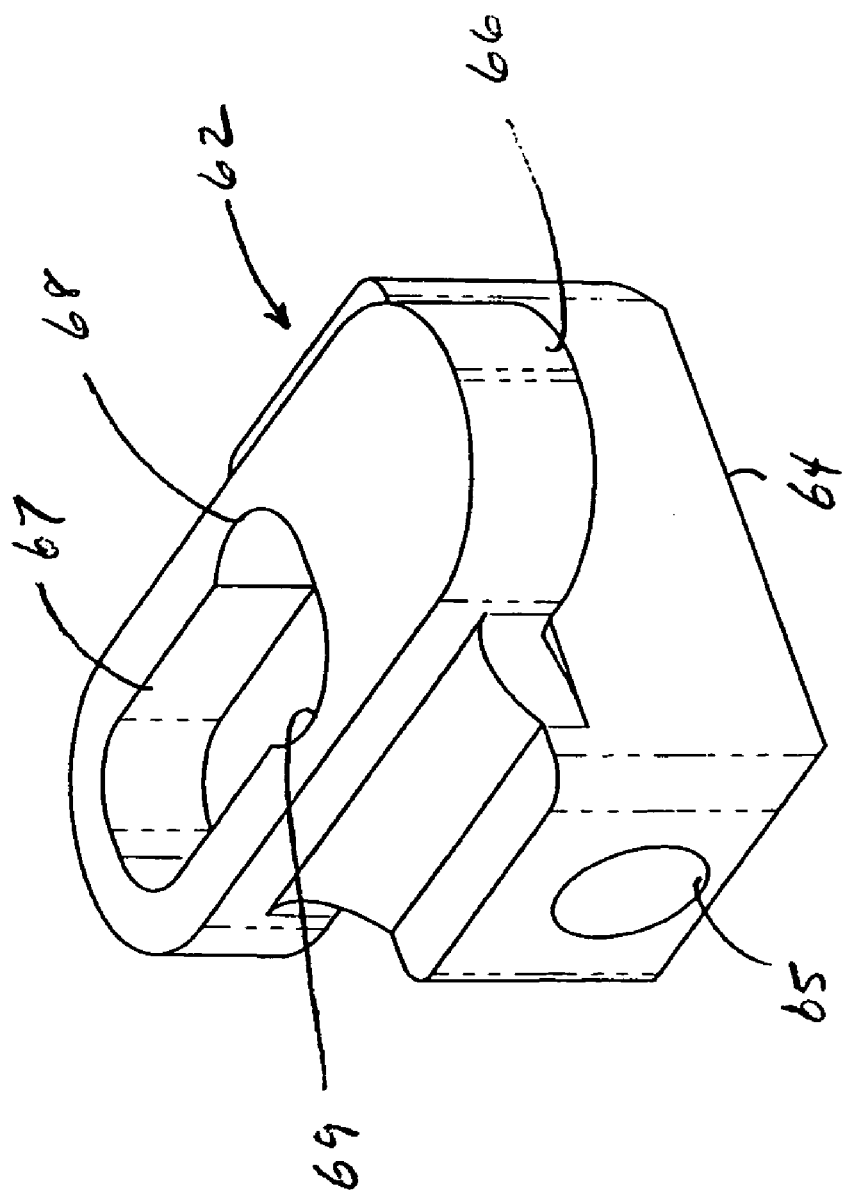
FIG. 9 is a perspective view of the slide of the device of FIG. 1 that is operably linked to the shaft assembly for deploying the expandable region of the shaft assembly into its expanded position.

As seen e.g. in FIGS. 4-7, device 10 includes separate actuating mechanisms for deploying the distal end of shaft assembly 40 into its expanded configuration and for moving clamping member 30 toward shaft assembly 40. Clamping member 70 and slide actuator 80 are independently operable. Slide actuator 80 includes head 82, shaft 81 and dial 84, and is rotatably mounted within housing 20. Shaft 81 is oriented in the housing perpendicular to shaft assembly 40. Dial 84 extends radially from shaft 81, with portions of the dial extending from housing 20 on either side of the housing at opening 19. Head 82 is received in and extends from recessed seat 21 of housing 20 and collar 29 of housing 20 receives shaft 81. Seat 21 and collar 29 maintain slide actuator 80 in place while allowing it to freely rotate. Dial 84 is further provided with underside recess 85 and pin 86 extending into the recess, more clearly shown in FIG. 10A. As shown in FIGS. 9 and 11, slide 62 includes base 64 with channel 65, and upper platform 66 containing slot 67. Control rod 41 is received through channel 65 and secured to the slide. Alternatively, the slide can be integrally formed with the control rod. Upper platform 66 and slot 67 are oriented both perpendicular to base 64 of slide 62 and normal to shaft 81 of slide actuator 80. Pin 86 is received and translatable within slot 67, such that rotation of dial 84 causes linear translation of slide 62 via pin 86. In this manner, slide 62 can be translated away from the distal end of the shaft assembly until the shaft assembly is in the fully open or deployed condition. Further, slot 67 includes notches 68 and 69 which receive the pin when the shaft assembly is in the deployed or non-deployed positions, respectively. A threshold rotational force is required to move the pin into slot 67 from either of these two positions. In this manner, the shaft assembly can be locked into either the open, deployed, or the closed, non-deployed position.

As seen e.g. in FIGS. 4-7, clamping member actuator 70 is likewise rotatably mounted within housing 20 and includes shaft 71 and turn knob 72. Shaft 71 is received in opening 22 of housing 20 and retained in place by flanges 75 and 76 that extend from shaft 71. Shaft 71 includes threaded portion 74 which threaded onto nut 77. Nut 77 in turn is received through slot 33 of clamping member 30 and is also slidably retained in groove 23 of housing 20 which is oriented parallel to the axis of shaft 71. Rotation of shaft 71 results in axial movement of nut 77 along the shaft, which is translated into pivotal movement of clamping member 30 about pivot pin 31.

Figure 12:
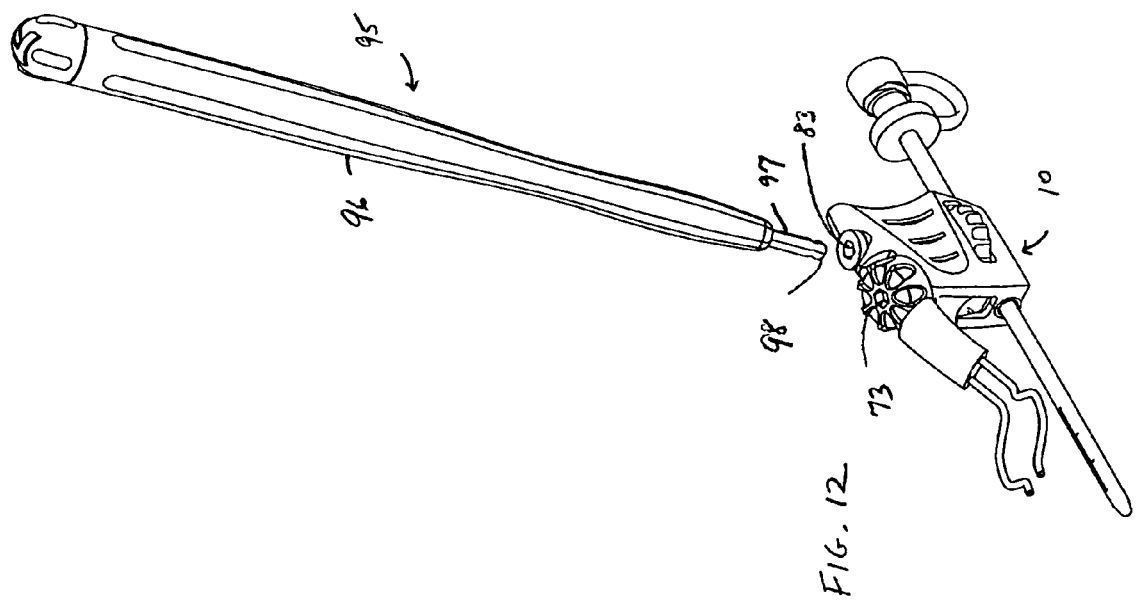
FIG. 12 is a perspective view of the device of FIG. 1 together with a tool for remote actuation of the device.

As seen in e.g. FIGS. 1-3, slide actuator 80 and clamping member actuator 70 are configured for both manual and remote manipulation. Rotation of slide actuator 80 and clamping member actuator 70 can be accomplished by manual rotation of dial 84 and turn knob 72, respectively. Alternatively, slide actuator 80 and clamping member actuator 70 are proved with hexagonal sockets 83 and 73, respectively. Socket 83 of slide actuator 80 is located in head 82 of the actuator and aligned with the axis of shaft 81. Similarly, socket 73 of clamping member actuator 70 is located in turn knob 72 itself and is aligned with the axis of shaft 71. As shown in FIG. 12, actuator tool 95, which consists of handle 96, with shaft 97 having head 98 extending therefrom, can be used to remotely actuate the device. Head 98 of tool 95 is configured to engage with sockets 73 and 83. Use of the actuator tool is especially useful to allow actuation of the device in a crowded surgical field where manual actuation may be difficult.

As also shown in e.g. FIGS. 4-7, device 10 includes bleed back tube 91 in fluid communication with lumen 42 of control rod 41. Ports 43 and 44 are in fluid communication with lumen 42 and exit to the exterior of control rod 41 at the expandable region of the shaft assembly. Tube 91 terminates at luer lock 92 which is capped with plug 93 connected to tube 91 through strap 94. In use, observance of a backflow of blood from the bleed back tube confirms that the deployed shaft assembly is positioned within the lumen of the target blood vessel. Further, when the device is activated, the suspension of blood blackflow serves as an indicator to the user that an effective seal has been created. In this manner, the user can check for adequacy of sealing before proceeding with a grafting procedure. Observance of continued bloodflow after activation can be attributable to a poor seal due to e.g. plaque or other defects or anomalies at the target site. The user can then deactivate the device and move to a different target location.

In addition, tube 91 also provides an avenue for injecting therapeutic or other materials into vessel, through ports 43 and 44 which again are in fluid communication with lumen 42.

Figure 13:
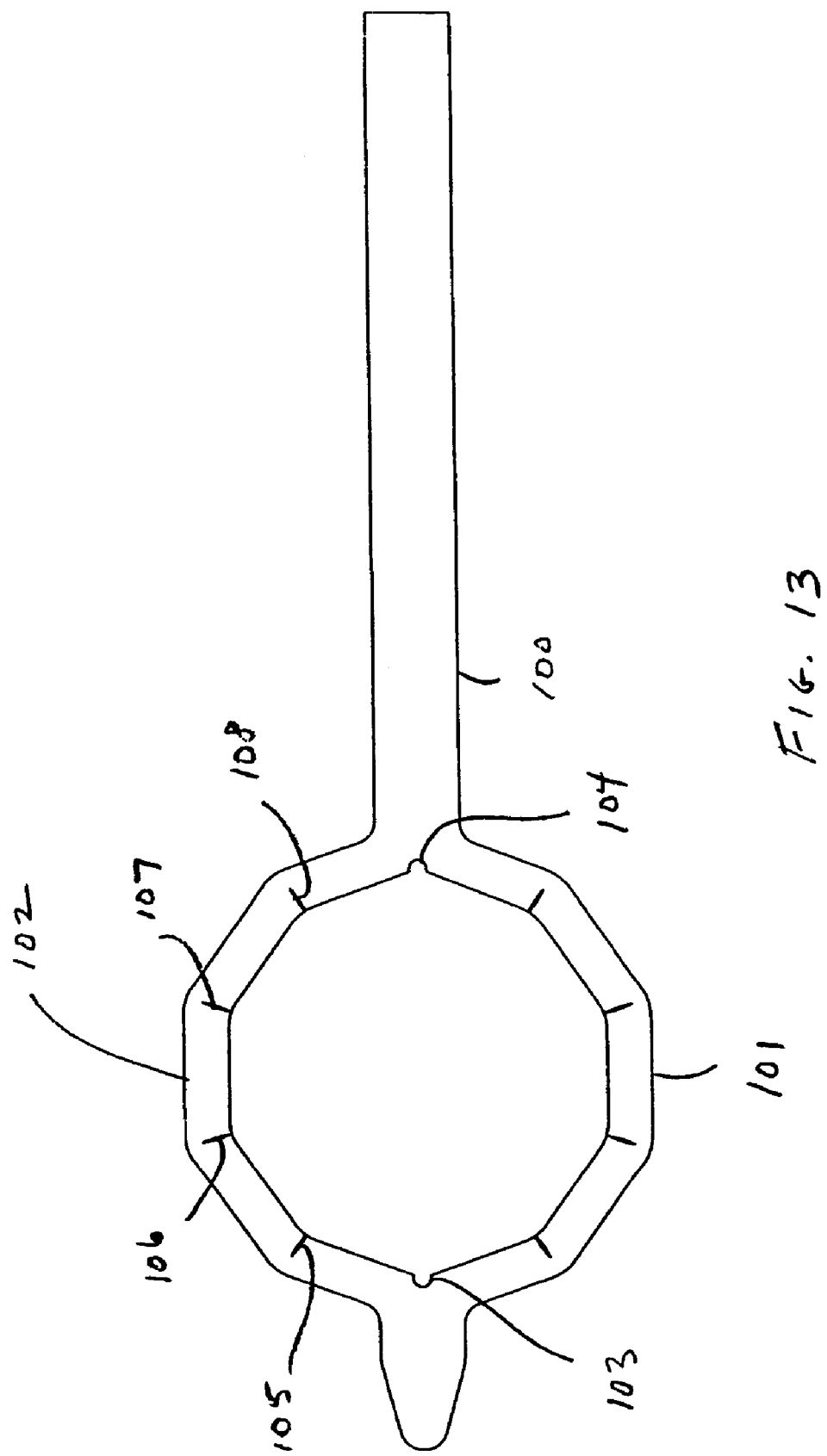
FIG. 13 is a top view of a shaft assembly of a device according to another embodiment the invention its deployed, expanded position.
Figure 14:
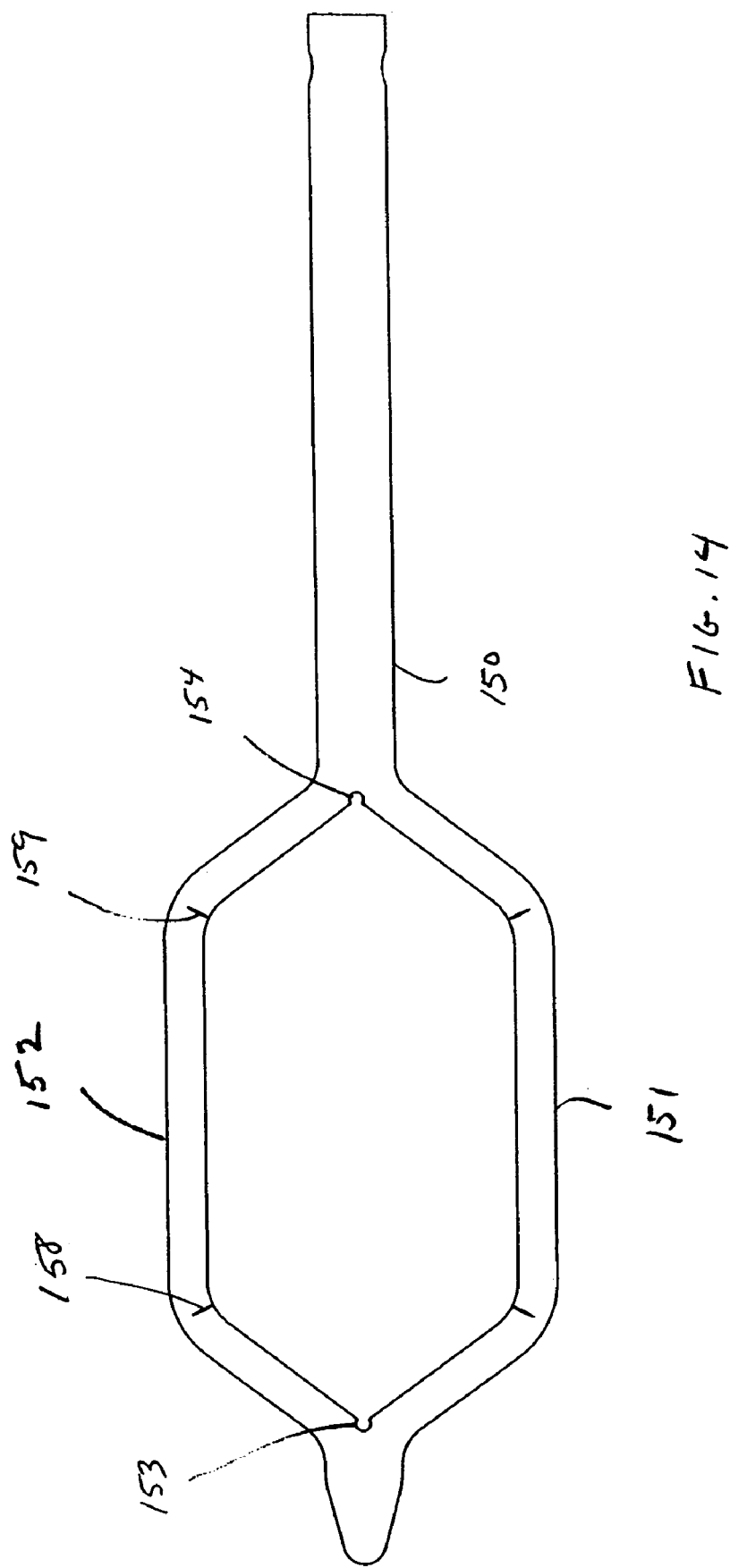
FIG. 14 is a top view of a shaft assembly of a device according to yet another embodiment the invention its deployed, expanded position.

In the embodiment of FIGS. 1-12, the deployed, expanded shaft assembly takes on a hexagonal configuration. The invention contemplates other configurations that would be readily discernable to one of skill, provided they provide a contiguous sealing area suitable for use in performing anastomosis procedures. In variations of the present invention, the expanded shaft assembly will be of a configuration that provides for a sealed area that is large enough to accommodate multiple anastomoses. Examples of such variations include those depicted in FIGS. 13 and 14. FIGS. 13 and 14 depict flexible tube 100 and 150, respectively, which like flexible tube 50 can be incorporated into a shaft assembly for a device according to the present invention. As shown, tube 100 of FIG. 13 includes bowing portions 101 and 102 deployed into an octagonal shape. This shape is achieved by including four notches 105-108 evenly spaced between distal hole 103 and proximal hole 104. Similar to the embodiment of FIGS. 1-11, notches 105-108 are further configured to ensure formation of the octagonal pattern, with the respective sides of each notch cut at an angle to one another such that as bowing portions 101 and 102 move outwardly, the sides of the notches come into contact with one another, maintaining the bowing portions at prescribed angles to form an octagon. Tube 150 of FIG. 14 includes bowing portions 151 and 152 deployed into an extended hexagonal shape. Similar to the embodiment of FIGS. 1-11, this shape is achieved by providing notches 158 and 159 between distal hole 153 and proximal hole 154, although with notches 158 and 159 being located closer to hole 153 or 154, respectively, than each other, such that the sides of the hexagon parallel to the shaft are elongated relative to the other sides. Other possible shapes include circular or oval shapes, which in the case of flexible tubes as in the embodiments of FIGS. 1-14, can be produced e.g. by varying the notching patterns in the bowing portions. In addition, any of these shapes can be adjusted to provide for sealed areas that are sufficiently large enough to accommodate multiple grafting sites. For example, the extended hexagonal shape of FIG. 14 can accommodate multiple grafting sites. As further detailed below, this greatly facilitates multiple anastomosis procedures. A single deployment of the sealing devices creates a sealed area large enough for multiple grafts without the need for further repositioning or redeployment of the device.

As mentioned, devices according to the present invention are designed for use, e.g., in an off-pump procedure, with the heart beating and blood flowing through the aorta. The shaft assembly is inserted into the aorta at a location remote from the desired anastomosis site(s) via an introduction hole created in the aorta according to known methods. Punch hole(s) or aortotomy(ies) are formed at the desired graft (anastomosis) site or sites, using e.g. an arterial punch, either before or after the shaft assembly is internally advanced to the desired site or sites and deployed. More typically, the hole(s) or aortotomy(ies) are created after the device is deployed and a seal is created. Once the device is positioned, it is actuated to deploy the shaft assembly into its expanded, deployed condition and to clamp the clamping member down onto the expanded region of the shaft assembly, creating a sealed area between the sealing membrane of the expanded shaft assembly region and the vessel wall. Once the seal is created, the graft(s) can be sutured or otherwise attached to the desired site(s), including through the use of automatic suturing devices known in the art. When the procedure(s) are complete, the device is returned to its non-deployed, non-clamping configuration and removed from the introduction hole, and the hole is sealed.

Figure 15:
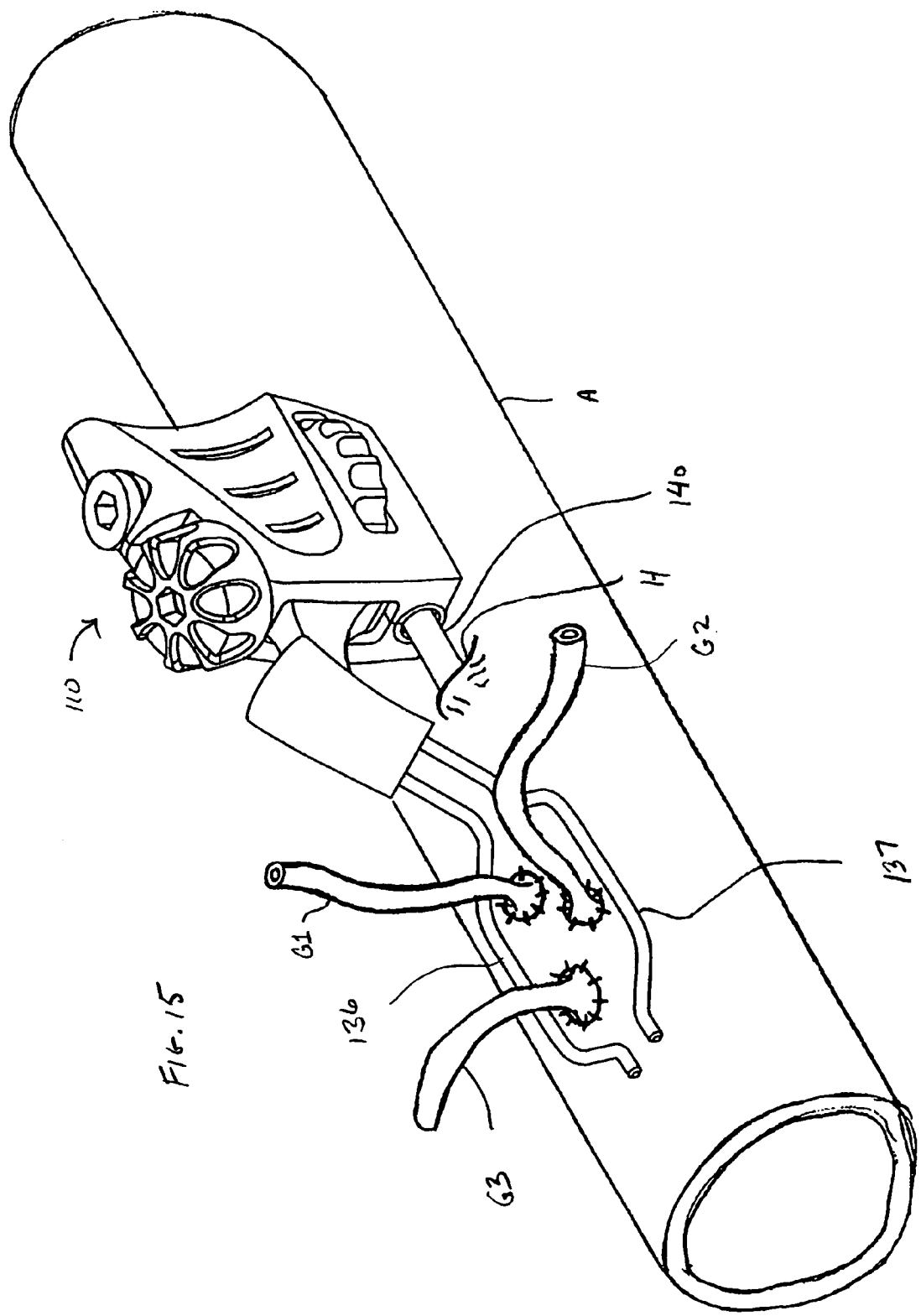
FIG. 15 is a perspective view of a device according to an embodiment of the invention in use to create a seal in a blood vessel for performing multiple anastomoses.

FIG. 15 shows an embodiment of the invention in use for performing such a procedure, and in particular, where the single deployment of the device provides a seal over an area of the vessel that allows for the performance of multiple anastomoses. Device 110 is similar to previously described device 10 but includes shaft assembly 140 that includes flexible tube 150 that forms an elongated hexagonal configuration as shown in FIG. 14. Forks 136 and 137 of clamping member 30 are correspond to the elongated hexagonal configuration of flexible tube 150 in its expanded configuration. As shown in operation, shaft assembly 140 has been inserted into hole H created in aorta A and actuated, creating a sealed area within the vessel that corresponds to the area encompassed by forks 136 and 137. As depicted, the sealed area is large enough to accommodate three separate grafts, G1, G2 and G3 without the need to move, reactuate or otherwise redeploy device 110. Thus multiple anastomoses can be performed with a single placement and actuation of device 110. Alternatively, multiple anasotomoses can be performed using devices according to the present invention simply by repositioning the expandable region at different desired sites but without removing the shaft assembly entirely from the vessel.

Figure 16:
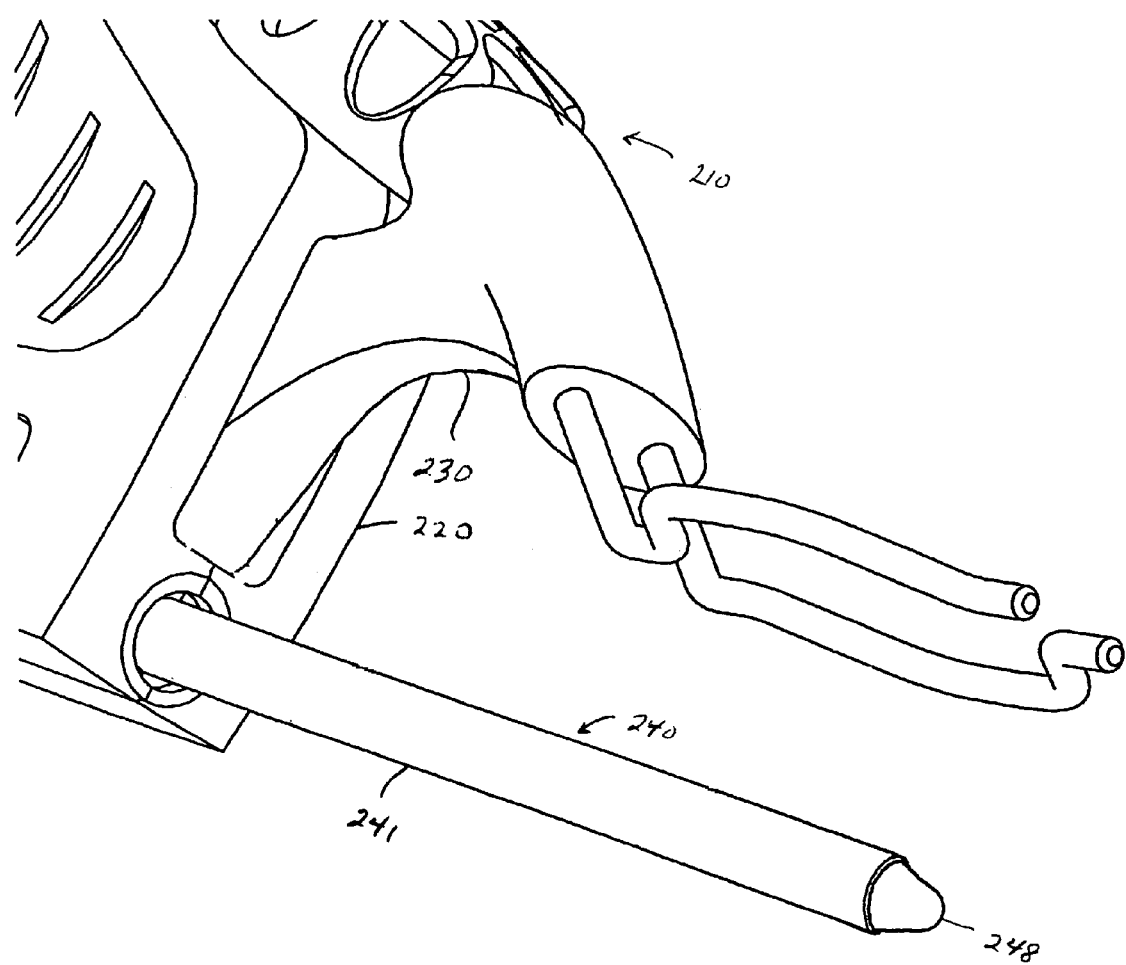
FIG. 16 is a perspective view of a shaft assembly of a device according to a further embodiment of the invention in its non-deployed position.
Figure 17:
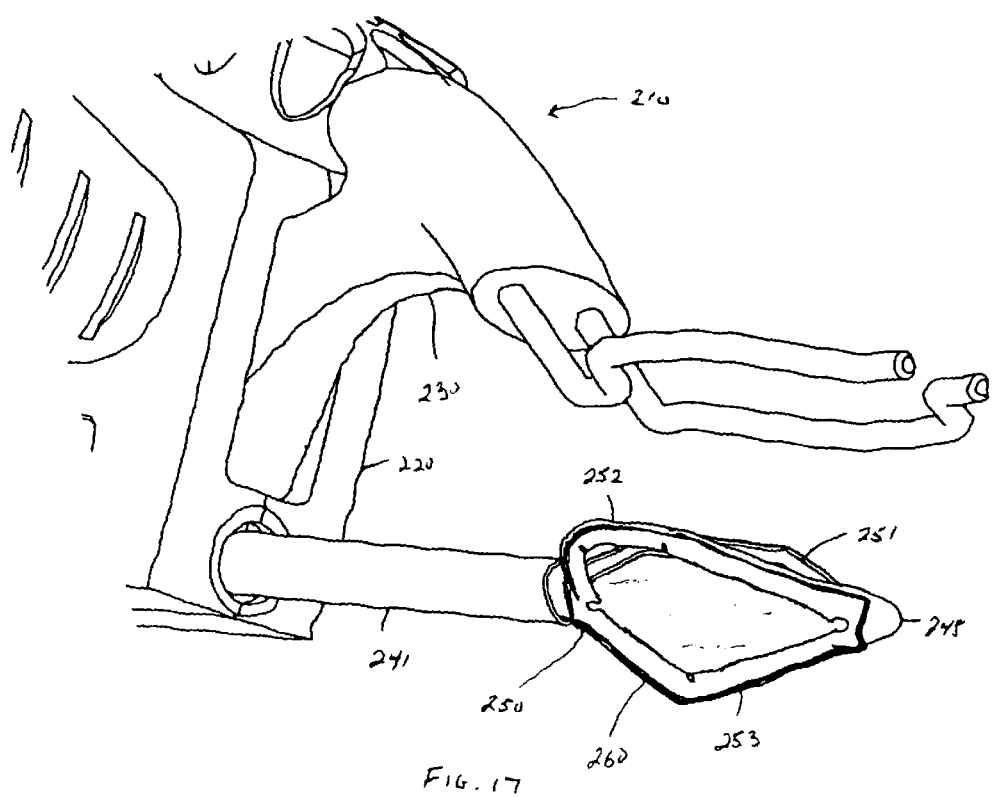
FIG. 17 is a perspective view of a shaft assembly of FIG. 16 in its deployed, expanded position.

FIGS. 16 and 17 show an alternative embodiment of the invention. Device 210 is similar in many aspects to device 10, but varies in the deployment of the expandable region. Shaft assembly 240 includes expandable shaft 250 encased in deployment tube 241. Expandable shaft 250 is formed of a shape memory super-elastic alloy at its distal end region that can be deformed and retained with tube 241 but which is configured to deploy and provide an expandable region upon release from tube 241. Retraction of tube 241 thus releases shaft 250 and deploys the expandable region, which consists of three bowing portions 251, 252 and 253, with elastomeric membrane 260 spanning the regions between 252 and 253 and between 253 and 251. Further, bowing region 253 expands in a direction away from clamping member 230. In use, this creates an expanded region having a cup-like configuration that creates the seal, and provides additional space for the user to suture the graft with less risk of puncturing or tearing the membrane. Tube 241 is configured to be rectratable relative to shaft 250 from the closed, non-deployed condition of FIG. 16 to the open, deployed condition of FIG. 17. This can be accomplished, e.g., by configuring housing 220 of the device to receive tube 241 and allow for translational movement of tube 241 relative to the housing and the fixed shaft 250. Similar mechanisms as used in device 10 can be adapted to actuate tube 241, for example, tube 241 can be secured to a slide similar to slide 62 of device 10 and a similar slide actuation member can be used to cause movement of the slide and tube relative to the shaft and thus deployment of the expandable region.

Figure 19A:
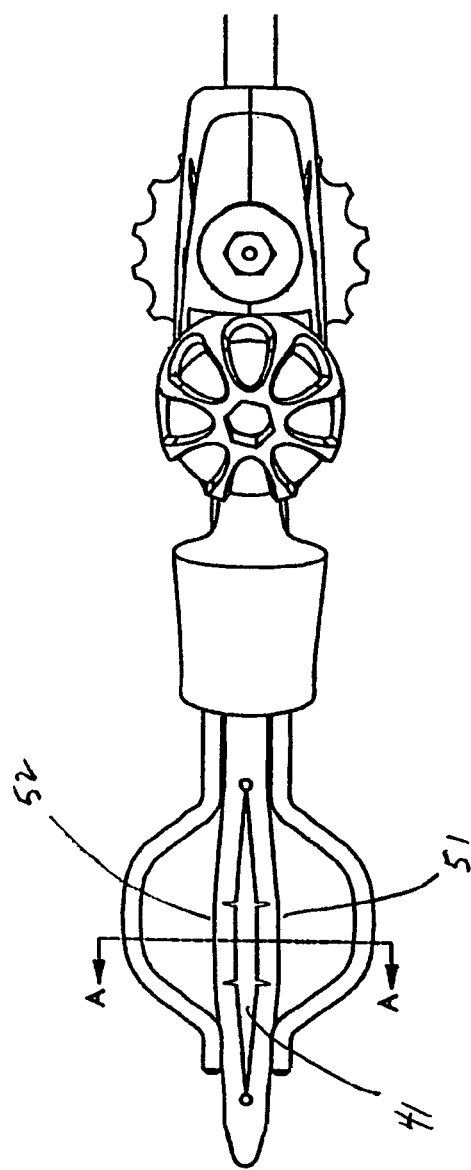
Figure 19A:
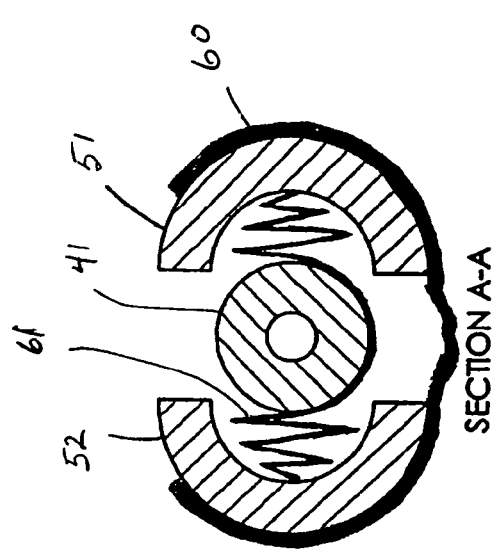
Figure 20A:
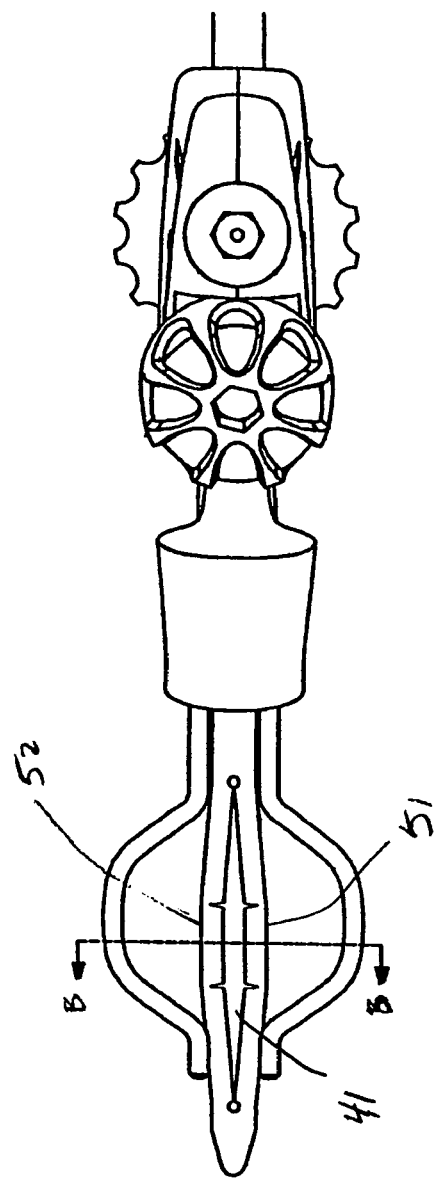
FIGS. 20A and 21A are top and sectional views, respectively, of a shaft assembly of a device according to a yet another embodiment of the invention in its non-deployed position, with FIG. 21A taken along plane B-B of FIG. 20A.
Figure 21A:
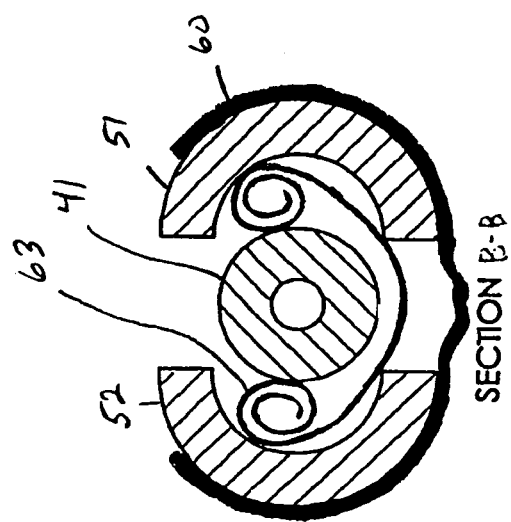
Figures 20B, 21B:
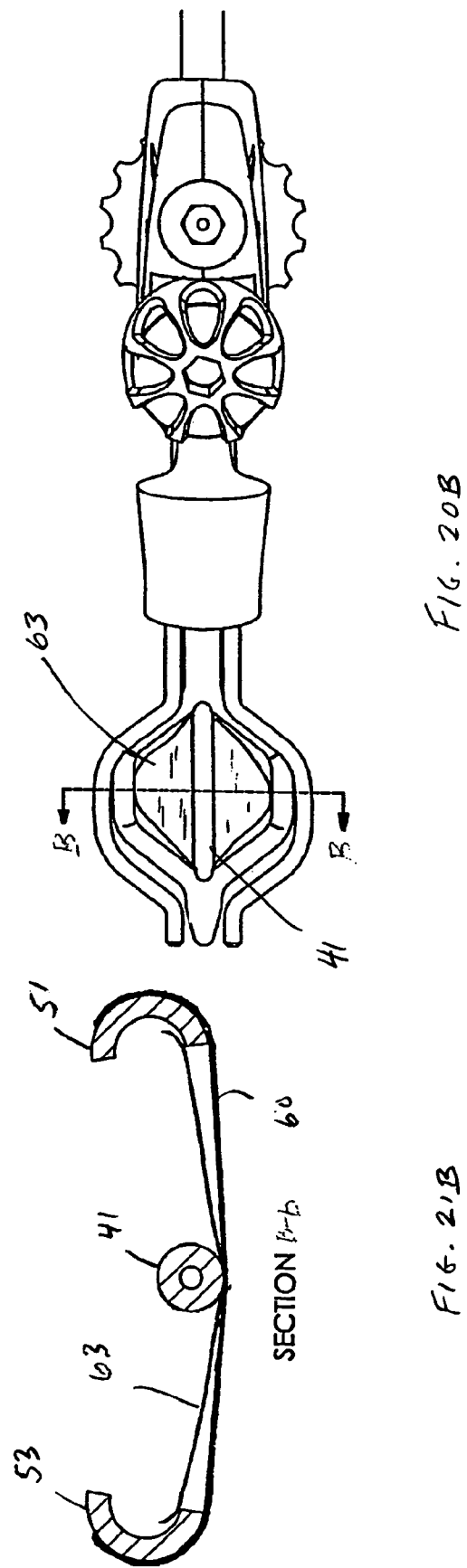
FIGS. 20B and 21B are top and end views, respectively, of the shaft assembly of the device of FIGS. 20A and 20A, in its deployed, expanded position, with FIG. 21B taken along plane B-B of FIG. 20B.

FIGS. 18-21 depict additional embodiments of the inventions that provide further protection to the sealing membrane. In the embodiment of FIGS. 18-19, the mid region of protective sheet 61 is translatable along control rod 41 and is secured at its edges to bowing portions 51 and 52 of flexible tube 50. Protective sheet 61 can be made of thin metal, plastic, or reinforced mesh material that is resistant to puncture. Protective sheet 61 is folded accordion-style in the non-deployed condition (FIG. 18A-19A), and then unfolds to cover the sealing membrane in the deployed condition (FIG. 18B-19B). In the embodiment of FIGS. 20-21, protective sheet 63 is slidably secured at its mid region along control rod 41, such that it can translate relative to the control rod, and is formed of a shape memory material again that is resistant to puncture. In the non-deployed condition (FIG. 20A-21A) sheet 63 adopts a configuration having two separate rolled-up sections on either side of rod 41. Upon deployment, the sheet unrolls to its natural configuration and covers the sealing membrane (FIG. 20B-21B). Other methods for protecting the sealing membrane against tear or puncture are also contemplated, including direct reinforcement of the membrane itself, including incorporation of reinforcing mesh into the membrane itself.

While particular embodiments of the invention have been described above, the invention is not intended to be limited to such, but rather one skilled in the art will recognize that many modifications may be made that still remain within the scope of the invention, as defined by the appended claims.

What is claimed as new and desired to be protected by Letters Patent of the United States is:

1. A device for creating a seal in a blood vessel comprising:
a low profile shaft assembly configured for insertion into a vessel, said shaft assembly having an expandable region at the distal end of the shaft assembly and a sealing membrane spanning said expandable region, said expandable region being deployable from a first low profile position to a second expanded position and having an area in its second expanded position;
a protective shield having a non-deployed and deployed state and being deployable over at least a portion of the expandable region in its second expanded position, said protective shield having a folded configuration in its non-deployed state and an unfolded configuration in its deployed state; and
a clamping member positioned generally opposite to and moveable towards said expandable region, said clamping member having a distal end shape corresponding to said expandable region in its second expanded position.

2. The device of claim 1 wherein said expandable region in its second expanded position has a hexagonal shape.

3. The device of claim 1 wherein said expandable region in its second expanded position has an octagonal shape.

4. The device of claim 1 wherein said expandable region in its second expanded position has an oval shape.

5. The device of claim 1 wherein said expandable region in its second expanded position has a circular shape.

6. The device of claim 1 wherein said expandable region further comprises segments that bow outwardly from the shaft assembly when the expandable region is deployed from said first low profile position to said second expanded position.

7. The device of claim 6 wherein at least two of the bowing segments are biased toward the clamping member when the expandable region is deployed from said first low profile position to said second expanded position.

8. The device of claim 6 wherein said bowing segments are formed of a slitted flexible tube.

9. The device of claim 6 wherein said bowing segments are formed of a super-elastic metal memory.

10. The device of claim 1 wherein the sealing membrane is reinforced.

11. The device of claim 1 wherein the shaft assembly further comprises a slide operably linked to said expandable region such that translational movement of the slide from a first to a second position deploys said expandable region from said first low profile position to said second expanded position.

12. The device of claim 11 wherein translational movement of the slide can be remotely actuated.

13. The device of claim 1 wherein the shaft assembly further comprises a deployment tube moveable in relationship to the expandable region such that translational movement of the deployment tube from a first to second position deploys said expandable region from said first low profile position to said second expanded position.

14. The device of claim 13 wherein translational movement of the deployment tube can be remotely actuated.

15. The device of claim 1 wherein said expandable region in its second expanded position corresponds to an area of a blood vessel that is large enough to accommodate multiple anastomosis sites.

16. The device of claim 1 wherein said expandable region in its second expanded position has a cup-shaped configuration.

17. A device for creating a seal in a blood vessel comprising:
a low profile shaft assembly configured for insertion into a vessel, said shaft assembly having an expandable region at the distal end of the shaft assembly and a sealing membrane spanning said expandable region, said expandable region being deployable from a first low profile position to a second expanded position and having an area in its second expanded position, said shaft assembly being housed within a deployment tube, the deployment tube being moveable in relationship to the expandable region such that translational movement of the deployment tube from a first to a second position deploys said expandable region from said first low profile position to said second expanded position; and
a protective shield that is deployed over at least a portion of the expandable region in its second expanded position; and
a clamping member positioned generally opposite to and moveable towards said expandable region, said clamping member having a distal end shape corresponding to said expandable region in its second expanded position.

18. The device of claim 17 wherein translational movement of the deployment tube can be remotely actuated.

19. The device of claim 17 wherein said expandable region in its second expanded position corresponds to an area of a blood vessel that is large enough to accommodate multiple anastomosis sites.

20. The device of claim 17 wherein said expandable region in its second expanded position has a hexagonal shape.

21. The device of claim 17 wherein said expandable region in its second expanded position has an octagonal shape.

22. The device of claim 17 wherein said expandable region in its second expanded position has an oval shape.

23. The device of claim 17 wherein said expandable region in its second expanded position has a circular shape.

24. The device of claim 17 wherein said expandable region in its second expanded position has a cup-shaped configuration.

25. The device of claim 17 wherein said expandable region further comprises segments that bow outwardly from the shaft assembly when the expandable region is deployed from said first low profile position to said second expanded position.

26. The device of claim 25 wherein at least two of the bowing segments are biased toward the clamping member when the expandable region is deployed from said first low profile position to said second expanded position.

27. The device of claim 25 wherein said bowing segments are formed of a slitted flexible tube.

28. The device of claim 25 wherein said bowing segments are formed of a super-elastic metal memory.

29. The device of claim 17 wherein the sealing membrane is reinforced.

30. The device of claim 17 wherein the shaft assembly further comprises a slide operably linked to said expandable region such that translational movement of the slide from a first to a second position deploys said expandable region from said first low profile position to said second expanded position.

31. The device of claim 30 wherein translational movement of the slide can be remotely actuated.

\* \* \* \* \*